US006194561B1

(12) United States Patent
Erlich et al.

(10) Patent No.: US 6,194,561 B1
(45) Date of Patent: Feb. 27, 2001

(54) CHARACTERIZATION AND DETECTION OF SEQUENCES ASSOCIATED WITH AUTOIMMUNE DISEASES

(75) Inventors: Henry A. Erlich, Oakland; Glenn T. Horn, Emeryville, both of CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 07/121,519

(22) Filed: Nov. 17, 1987

Related U.S. Application Data

(63) Continuation-in-part of application No. 06/899,512, filed on Aug. 22, 1986, now abandoned, and a continuation-in-part of application No. 06/899,344, filed on Aug. 22, 1986, now abandoned, which is a continuation-in-part of application No. 06/839,331, filed on Mar. 13, 1986, now abandoned.

(51) Int. Cl.[7] .................................................... C07H 21/04
(52) U.S. Cl. .......................................................... 536/24.31
(58) Field of Search ........................ 536/27, 24.3, 24.31; 435/6; 935/77, 78

(56) References Cited

U.S. PATENT DOCUMENTS

| 4,582,788 | 4/1986 | Erlich | 435/6 |
|---|---|---|---|
| 4,683,195 | 7/1987 | Mullis et al. | 435/6 |
| 4,683,202 | 7/1987 | Mullis | 435/91.2 |
| 4,965,189 | 10/1990 | Owerbach | 435/6 |
| 4,971,902 | 11/1990 | Nepom | 435/6 |
| 5,039,606 | 8/1991 | Nepon | 435/6 |
| 5,059,519 | 10/1991 | Owerbach | 435/6 |
| 5,110,920 | 5/1992 | Erlich | 536/24.31 |

FOREIGN PATENT DOCUMENTS

| 237362 | 9/1987 | (EP) . |
|---|---|---|
| 0314500 | 5/1989 | (EP) . |
| 8607464 | 12/1986 | (WO) . |

OTHER PUBLICATIONS

Brautbar et al., 1980, Tissue Antigens 16:238–243.
Ryder et al., 1981, Ann. Rev. Genet. 15:169–187.
Svejagaard, et al., 1983, *Immunol. Rev.* 70:193–218.
Donaich, et al., 1983, *Ann. Rev. Med.* 34:13–20.
Conner et al., Jan. 1983, *Proc. Natl. Acad. Sci. USA* 80:278–282.
Owerbach et al., Oct. 1984, *Diabetes* 33:958–965.
Kagnoff et al., Nov. 1984, *J. Exp. Med.* 160:1544–1557.
Trowsdale et al., 1985, *Immunol. Rev.* 85:4–43.
Cohen–Hauguenauer et al., May 1985, *Proc. Natl. Acad. Sci USA* 82:3335–3339.
Raffel et al., May/Jun. 1985, *Clinical Diabetes* 3:50–54.
Yoon et al., Sep–Oct. 1985, *Diabetes Care* 8(Supp. 1):39–44.
Stetler et al., Dec. 1985, *Proc. Natl. Acad. Sci. USA* 82:8100–8104.
Kim et al., Dec. 1985, *Proc. Natl. Acad. Sci. USA* 82:8139–8145.
Tait, et al., 1986, *Tissue Antigens* 28:65–71.
Oldstone et al., 1986, *Concepts in Viral Pathogenesis II* (ed. Notkins et al.), pp. 195–202.
Holbeck et al., 1986, *Immunogenetics* 24:251–258.
Gregersen et al., Apr. 1986, *Proc. Natl. Acad. Sci. USA* 83:2642–2646.
Eisenbarth, May 22, 1986, *N. Eng. J. Med.* 314(21):1360–1368.
Angelini et al., Jun. 1986, *Proc. Natl. Acad. Sci. USA* 83:4489–4493.
Scharf et al., Sep. 5, 1986, *Science* 233:1076–1078.
Sheldon et al., Dec. 1986, *Proc. Natl. Acad. Sci. USA* 83:9085–9089.
Henson et al., 1987, *Immunogenetics* 25:152–160.
McChesney et al., 1987, *Ann. Rev. Immunol.* 5:279–304.
Erlich et al., 1987, *Perspectives in Immunogenetics and Histocompatibility* 7:93–111.
Michelson et al., Apr. 1987, *J. Clin. Invest.* 79:1144–1152.
Acha–Orbea et al., Apr. 1987, *Proc. Natl. Acad. Sci. USA* 84:2435–2439.
Sette et al., Jul. 30, 1987, *Nature* 328:395–399.
Szafer et al., *Proc. Natl. Acad. Sci. USA* 84:6542–6545.
Oldstone et al., Sep. 11, 1987, *Cell* 50:819–820.
Niven et al., Oct. 3, 1987, *Lancet* pp. 805.
Todd et al., Oct. 1987, *Nature* 329:599–604.
Marx, Oct. 30, 1987, *Science* 238:613–614.
Gorski and Mach, 1986, *Nature* 322:67–70.
Erlich et al., 1984, *Banbury Reports* 16:321–331.
Long et al., 1983, *EMBO J.* 2:389–394.
Gorski et al., 1984, *Proc. Natl. Acad. Sci. USA* 81:3934–3938.
Owerbach et al., 1986, *Immunogenetics* 24:41–46.
Owerbach et al., 1983, *Nature* 303:815–817.

*Primary Examiner*—Robert A. Schwartzman
(74) *Attorney, Agent, or Firm*—Douglas A. Petry

(57) ABSTRACT

DNA sequences and corresponding amino acid sequences from the HLA class II beta region of the human genome that are associated with insulin-dependent diabetes mellitus (IDDM) and *Pemphigus vulgaris* (PV) have been identified. Specifically, marker DNA sequences which detect either directly or indirectly the identity of the codon encoding for the amino acid at position 57 of the DQβ protein sequence are disclosed as well as sequences from the DRβ region. These sequences may be used to generate DNA hybridization probes and antibodies for assays to detect a person's susceptibility to autoimmune diseases, such as IDDM and PV. Such antibodies and peptides encoded by said DNA sequences can be used therapeutically or prophylactically.

40 Claims, 8 Drawing Sheets

Sequence of the PCR amplified DR-beta segment

```
       |----------GH46----------->
   1   CCGGATCCTTCGTGTCCCCAGACCACGTTTCTTGGAGCAGGTTAAACATGAGTGTCATTT
       ------                     |----> EXON 2
       Bam H-I

61   CTTCAACGGGACGGAGCGGGTGCGGTTCCTGGACAGATACTTCTATCACCAAGAGGAGTA

121   CGTGCGCTTCGACAGCGACGTGGGGGAGTACCGGGCGGTGACGGAGCTGGGGCGGCCTGA

|-------GH78-------|
 181   TGCCGAGTACTGGAACAGCCAGAAGGACATCCTGGAAGACGAGCGGGCCGCGGTGGACAC

Pst I
       ------
 241   CTACTGCAGACACAACTACGGGGTTGTGGAGAGCTTCACAGTGCAGCGGCGA
             <----------GH50----------|
```

Sequence of the PCR primers

GH46: CCGGATCCTTCGTGTCCCCACAGCACG  27-mer

GH50: CTCCCCAACCCCGTAGTTGTGTCTGCA  27-mer

Sequence of the Dw10 sequence specific oligomer

GH78: GACATCCTGGAAGACGAGC  19-mer

FIG. 1

DR Beta-I SEQUENCES

```
                        10         20         30         40         50         60         70         80         90
Dw4  Prototype   RFLEQVKHECHFFNGTERVRFLDRYFYHQEEYVRFDSDVGEYRAVTELGRPDAEYWNSQKDLLEQKRAAVDTYCRHNYGVGESFTVQRR  (DR4,w4)-I
Dw10 Prototype   ------------------------------------------------------------I--DE--------------------------  (DR4,w10)-I
Dw13 Prototype   ------------------------------------------------------------------R--E------V-------------  (DR4,w13)-I PATIENT I        ------------------------------------------------------------I--DE--------------------------  (DR4,w10)-I
                 ------------------------------------------------------------------R--E--------------------  (DR4,w13)-I PATIENT II       -----YSTS------------------N-----------F--------------------I--DE--------------------------  (DR4,w10)-I
                                                       E                    F--DR--                          (DR5)-I PATIENT III      -----YSTS------------------N-----------F--------------------I--DE--------------------------  (DR4,w10)-I
                                                       E                    F--DR--                          (DR5)-I DR5 prototype    -----YSTS------------------N-----------F--------------------E--DR--------------------------  (DR5)-I
```

DR5 Beta-III Sequences

```
DR5 Prototpye    -----LL-S------------------E-H-HN------A--------H----R---------------GQ--N----------------  (DR5)-IIIa
Patient II       -----LL-S------------------E-H-HN------A-------------R---------------GQ--N----------------  (DR5)-III
Patient III      -----LL-S------------------E-H-HN------A-------------R---------------GQ--N----------------  (DR5)-III
```

DR4 Beta-IV Sequences

```
DR4 Prototype    -----A-C----L------WN-I----N----A-YN---L----Q-----------------------RR--E-------Y---V-----  (DR4)-IV
Patient I        -----A-C----L------WN-I----N----A-YN---L----Q-----------------------RR--E-----------------  (DR4)-IV
Patient II       sequence not determined
Patient III      sequence not determined
```

FIG. 2

Alignment of HLA DQ-beta Protein Sequences

```
Exon-2:       10        20        30        40        50        60        70        80        90
DCB4: DFVYQFKGMCYFTNGTERVRLVTRYIYNREEYARFDSDVGVYRAVTPLGPPAAEYWNSQKEVLERTRAELDTVCRHNYQLELRTTLQRR  (DR4)
  JS: ------------------------------------------------------------------------------------------  (DR4,4)*    DQB3.2    3
  VW: ------------------------------------------------------------------------------------------  (DR4,7)*
 JNP: ------------------------------------------------------------------------------------------  (DR4,3)*
 JOP: ------------------------------------------------------------------------------------------  (DR4,3)*
MMCC: ------------------------------------------------------------------------------------------  (DR4,3)*
 KOZ: ---------------------------------------D-------------------------------------------------  (DR9)
DQB37: --------A-------------Y-----------------E-------------D-----------------------------------  (DR4)
 NIN: ----------------------Y-----------------E-------------D-----------------------------------  (DR4)
 JHA: ----------------------Y-----------------E-------------D-----------------------------------  (DR4)
 LUY: ----------------------Y-----------------E-------------D-----------------------------------  (DR8)
 JGL: ----------------------Y-----------------E-------------D-----------------------------------  (DR5)
 JME: ----------------------Y-----------------E-------------D-----------------------------------  (DR5)
  DC: ----------------------Y-----------------E-------------D-----------------------------------  (DR4,1)*   DQB3.1    3
  JR: ----------------------Y-----------------E-------------D-----------------------------------  (DR4,1)*
 KT3: -----F--------------L-G-----------------------------------RLD-----DI--ED--SV---------------  (DR4)
 ARC: --------------------L-G---------------------------------RLD-----DI--ED--SV---------------  (DR8)      DQB4     1
 OLN: --------------------L-G---------------------------------RLD-----DI--ED--SV---------------  (DR8)
  MZ: --------------------L-G-----------------EF----L--L---------RLD-----DI--ED--SV---------------  (DR8,7)*
WT49: ------------------------S-S-------IV---------------------------DI--K--AV--R---------------  (DR3)
```

Alignment of HLA DQ-beta Protein Sequences

FIG. 5A

Alignment of HLA DR-beta Protein Sequences

Alignment of HLA DR-beta Protein Sequences

```
CR#4:    ---LR-S---------Y-----HN----FL-------V--S----------GR--N--       (DR8,1)-III *
CM#15:   ---YSTS---------Y-------HN----N-------F---------I--DE----------- (DR6,3)-I   *
DRBM2:   -YSTS-----------Y-------HN----N-------F---------I--DE----------- (DR6)-I
WVD#8:   ---YSTS-------K-Y-------HN----N-------F---------I--DE--------V-- (DR6)-I
DD#6:    ---YSTS---------Y-------HN----N-------F---------I--DE----------- (DR6,3)-I   *
DRBP3:   ---YSTS---------Y-------HN----N-------F---------------GR--N----- (DR3)-I
DRBB2:   ---YSTS---------Y-------HN----N-------F---------------GR--N--V-- (DR3)-I
CM#5:    ---YSTS---------Y-------HN----N-------F---------------GR--N--V-- (DR3,6)-I
DRBO4:   ---YSTS---------Y-------HN----N-------F---------------GR--N--V-- (DR3,4)-I
604#4:   ---YSTS---------Y-------HN----N-------F---------------GR--N--V-- (DR3,4)-I
DD#7:    ---YSTS---------Y-------HN----N-------F---------------GR--N----- (DR3,6)-I
QBL#3:   ---YSTS---------Y-------HN----N-------F---------------GR--N----- (DR3)
AVL#2:   ---YSTS---------Y-------HN----N-------F---------------GR--N----- (DR3)-I
HAR#3:   ---YSTS---------Y-------HN----N-------F---------------GR--N----- (DR3)-I
DRBR1:   ---YSTS---------------------N-------E---F--DR------------------- (DR3)-I
DRBS8:   ---YSTS---------------------N-------E---F--DR------------------- (DR5)-I
DRBM7:   -W-YSTG---Y----------------N--------S---F--DR--L---------------- (DR5)-I
CR#6:    ---YSTG---Y----------------N--------S---F--DR--L---------------- (DR8)
HR#3:    ---YSTG---Y----------------N--------S---F--DR--L---------------- (DR8,1)     *
TAB#2:   ---YSTG---Y----------------N--------S---F--DR--L---------------- (DR8,5)     *
DRBM3:   ---YSTS---------HN----------------------I--DR--L---------------- (DR8)-I
DRBB11:  --Q-D-Y--------H-DI-N---DL--------------A-DD-----RR--E--------V- (DR6)-I
DRBL2:   --Q-D-Y--------H-GI-N----N--------------F--DR------------------- (DR2,Dw2)-I
DRBL4:   --Q-D-Y--------H-GI-N----N--------------F--DR------------------- (DR2,Dw12)-I
DRBL6:   ---Q-D-Y-------H-GI-N----N------------I--A------------------AV-- (DR2,'AZH')-I
DRBH1:   ---W-P-R-------L-E-CI-N--S--------------I--A--------------------- (DR2,Dw2)-III
DRBB6:   ---W-P-R-------L-E-CI-N--S------------I--A-------------------V-- (DR2,Dw12)-III
DRBB5:   ---W-P-R-------L-E-CI-N--S--------------F--DR------------------- (DR2,Dw12)-III
DRBC:    ---W-L-F-------L-E-CI-N--S----------E---------R----------------- (DR2,MN2)-III
JR#14:   ---W-L-F-------L-E-CI-N--S----------L---------R----------------- (DR1)-I
DC#7:    ---W-L-F-------L-E-CI-N--S---K----------------R----------------- (DR1,4)-I
BG#1:    --W-L-F--------L-E-CI-N--S---R----------I-DE-------------------- (DR1,4)-I   *
CR#2:    --W-L-F--------L-ELFI-N----------------------R------------------ (DR1,1)-I   *
DRBW1:   -S-W-L-F-----?--L-E-RVHN----A-Y--------------------------------- (DR1,8)-I   *
DRBP4:   ----E--F-------L-E-RVHN----N-------------------RR--------------- (DR1)
DRBM6:   ---K-D-F-------Y-H-GI-N----N-----------------F--RR--EL--V------- (DR12,3)
DRBS9:   ---------------Y-H-GI-N---------------V--S----F--RR--E---V------ (DR9)
DRBS10:  ---W-G-YK-----Q--E-L--N----F----------V--S---I--DR-GQ---V------- (DR7)
DRBK1:   ---W-G-YK-----Q--E-L--N----F----------V--S---I--DR-GQ----------- (DR7)-I
```

FIG. 5B

CHARACTERIZATION AND DETECTION OF SEQUENCES ASSOCIATED WITH AUTOIMMUNE DISEASES

CROSS-REFERENCE TO RELATED APPLICATIONS

This application is a continuation-in-part application of now abandoned U.S. Ser. No. 899,512 filed Aug. 22, 1986 and of now abandoned U.S. Ser. No. 899,344 filed Aug. 22, 1986, which is a continuation-in-part application of now abandoned U.S. Ser. No. 839,331 filed Mar. 13, 1986.

BACKGROUND OF THE INVENTION

A variety of autoimmune diseases have been associated with serologically defined variants of the human leukocyte antigen (HLA) class III antigens. The HLA region, located on the short arm of chromosome 6, encodes many different glycoproteins that have been classified into two categories. The first category, class I products, encoded by the HLA-A, -B, and -C loci, are on the surface of all nucleated cells and function as targets in cytolytic T-cell recognition. The second category, class II products, encoded by the HLA-D region, are involved in cooperation and interaction between cells of the immune system. These class II products appear to be encoded by at least three distinct loci, DR, DQ and DP, each with its distinct alpha and beta chains. The class II loci of the human major histocompatibility complex (MHC) encode highly polymorphic cell-surface glycoproteins (macrophage and β-cell transmembrane glycoproteins). [For review article, see Giles et al. *Adv. in Immunol.* 37:1–71 (1985).] The polymorphism in class II antigens is localized to the $NH_2$-terminal outer domain and is encoded by the second exon. The class II polymorphic residues have been postulated to interact with the T-cell receptor or with foreign antigen or both [Sette et al., *Nature*, 328:395–399 (1987)] with recognition of the antigen peptide fragments in association with a specific class II product leading to T cell activation and consequent stimulation of antibody production by β lymphocytes [Marx et al., *Science*, 238:613–614 (1987).]

This invention relates to HLA class II beta genes and proteins associated with autoimmune diseases and methods for their diagnostic detection. Specifically, the autoimmune diseases on which this invention focuses are insulin-dependent diabetes mellitus (IDDM) and *Pemphigus vulgaris* (PV).

Insulin-dependent diabetes mellitus (IDDM), a chronic autoimmune disease also known as Type I diabetes, is a familial disorder of glucose metabolism susceptibility associated with specific allelic variants of the human leukocyte antigens (HLA). The dysfunctional regulation of glucose metabolism occurring in IDDM patients results from the immunologically mediated destruction of the insulin-producing islet cells of the pancreas, the beta cells. The development of IDDM can be divided into six stages, beginning with genetic susceptibility and ending with complete destruction of beta-cells. G. Eisenbarth, *N. Eng. J. Med.*, 314:1360–1368 (1986). [Donaich et al., *Annu. Rev. Med.*, 34:13–20 (1983).]. More than 90% of all IDDM patients carry the DR3 and/or DR4 antigen, and individuals with both DR3 and DR4 are at greater risk than individuals who have homozygous DR3/3 or DR4/4 genotypes. L. Raffel and J. Rotter, *Clinical Diabetes*, 3:50–54 (1985); Svejgaard et al., *Immunol. Rev.*, 70:193–218 (1983); L. Ryder et al., *Ann. Rev. Genet.*, 15:169–187 (1981).

Pemphigus derived from the Greek pemphix meaning blister or pustule is the name applied to a distinctive group of chronic or acute skin diseases characterized by successive crops of itching bullae. *Pemphigus vulgaris* (PV) is a rare relapsing disease manifested by suprabasal, intraepidermal bullae of the skin and mucus membranes, which is invariably fatal if untreated; however, remission has been obtained by the use of corticosteroid hormones and immunosuppressive drugs. PV, an autoimmune disease, has been strongly associated with the HLA serotypes DR4 and DRw6 [Brautbar et al., *Tissue Antigens*, 16:238–241 (1986)] with less than 5% of PV patients possessing neither marker. Disease associations with two different haplotypes can be interpreted to mean (1) the two haplotypes share a common allele or epitope, or, alternatively, that (2) different alleles on the two haplotypes are capable of conferring disease susceptibility.

Molecular analysis of the HLA class II genes has revealed that the HLA serotypes are genetically heterogeneous, and that, in particular, the DR4 haplotype consists of five different DRβI allelic sequences corresponding to the five mixed lymphocyte culture (MLC) defined types Dw4, Dw10, Dw13, Dw14 and Dw15 [Gregersen et al., PNAS (USA) 83:2642–2646 (1986)] and three different DQβ allelic sequences corresponding to the DQβ3.1, DQβ3.2 and DQ-blank types [Erlich et al., in Schacter et al. (eds.): *The Molecular Analysis of Histocompatibility Antigens*, pp. 93–109 (1987)]. Virtually all of the extensive polymorphism characteristic of the class II loci has been localized to the second exon.

Sequence analysis of coding sequence polymorphisms in the DRβ loci revealed that the sequence or epitope in the DR4 DRβI chain that distinguishes Dw10 from the other DR4 subtypes is shared by the DRβI chain of the DRw6 haplotype. [Gorski et al., *Nature*, 322:67–70 (1986)]. Recently, restriction fragment length polymorphisms (RFLPs) which subdivide the DR4 and DRw6 haplotypes were obtained by using a HLA-DQβ cDNA probe; such RFLPs have been reported to be even more highly associated with PV than are the serologic markers [Szafer et al., 1987, *Proc. Natl. Acad. Sci.* USA 84:6542–6545.].

Of all the immunologically defined polymorphisms, the HLA-DR beta region has been found to be most strongly associated with IDDM. Therefore, restriction fragments of the HLA class II-β DNA have been analyzed for use as genetic markers of insulin-dependent diabetes mellitus. D. Owerbach et al., *Diabetes*, 33:958–964 (1984); O. Cohen-Haguenauer et al., *PNAS* (USA), 82:3335–3339 (1985); D. Stetler et al., *PNAS* (USA), 82:8100–8104 (1985).

Arnheim et al., *PNAS* (USA), 82:6970–6974 (October 1985), examined DNA polymorphisms within the HLA class II loci associated with susceptibility to IDDM by using genomic blot-hybridization analysis with DQβ and DRβ cDNA probes. Described therein is a DQβ subdivision of the DR4 haplotype wherein one DR4 variant had a RsaI restriction fragment length polymorphism (RFLP) of 1.8 kb and another had a RsaI RFLP of 1.5 kb. The DQβ-related 1.5 kb RsaI fragment was reported to identify a number of non-DR4 IDDM individuals as well as 90% of all IDDM DR4 individuals.

Other investigators using other restriction enzymes (e.g., BamHI, HindIII) have reported RFLP subdivisions of the DR4 haplotype using DQβ probes. [Holbeck et al., *Immunogenetics* (1986) 24:251–258; Henson et al., *Immunogenetics*, (1987) 25:152–160).] Holbeck et al., id., found that the RFLP subsets of DR4, designated DQw3.1 and DQw3.2 are distinguishable by the reactivity of their expressed products with a specific monoclonal antibody TA10. [Kim et al., *PNAS* (USA), 82:8139–8142 (1985); Tait et al., *Tissue Antigens*, (1986) 28:65–71.] The DQw3.1 subtype correlates with the serologic specificity TA10⁺, whereas DQw3.2 correlates with TA10⁻.

Now abandoned U.S. Ser. No. 899,344 (filed Aug. 22, 1986) entitled "Process for Detecting Specific Nucleotide Variations and Genetic Polymorphisms Present in Nucleic Acids" (incorporated herein by reference) discloses the cloning and sequencing of the RsaI 1.5 kb (DQw3.2) and the RsaI 1.8 kb (DQw3.1) variants of DR4 haplotypes and illustrates the differences in the sequences thereof. (Such differences are shown herein in Tables III and IV.)

WO 86/07464 discloses a specific $DQ\beta_2$ allelic variant, DQw3.2 as a specific genomic marker associated with IDDM, and provides two methods of identifying individuals at increased risk of diabetes. The first method involves the use of a labeled probe to detect the DQw3.2 allele, whereas the second method involves the serologic detection of the DQw3.2 allele.

Erlich et al., in Schacter et al., (eds.), *Perspectives in Immunogenetics and Histocompatibility*, Vol. 7:93–106 (1987), reported the protein translation sequences for the DQw3.1 and 3.2 variants.

Michelson et al., *J. Clin. Invest.*, 79:1144–1152 (April 1987), reported the nucleotide sequence for the DQw3.1 variant.

Acha-Orbea et al., *PNAS* (USA), 84(8):2435–2435 (1987) reported on differences in the H-2 I-A region of control mice and diabetes-susceptible NOD (non-obese diabetic) mice. Normal mice have an aspartate residue at position 57 of said region whereas NOD mice have a neutral serine residue at that position. The human HLA-DQβ region is analogous to the H-2 I-A region of the mouse.

Yoon et al., *Diabetes Care*, 8 (suppl. 1):39–44 (September-October 1985), presents a review of the evidence for viruses as a trigger for IDDM in animals and humans. See also, Bodansky et al., *Lancet*, (1986), ii:1351–1353; Kagnoff et al., *J. Exp. Med.*, (1984), 160:1544–1557; McChesney et al., *Ann. Rev. Immunol.* (1987), 5:279–304; Oldstone et al., in Notkins et al. (eds.), *Concepts in Viral Pathogenesis* (1986); Schwimmback et al., *J. Exp. Med.* (1987), 166:173–181; Silver et al., *Disease Markers* (1985), 3:155–168; and Srinivasappa et al., *J. Virol.*, 57:397–401.

Roudier et al., Abstract from the American Rheumatism Association (Western Region) meeting in San Diego, Calif., Nov. 5–7, 1987, reported that the HLA Dw4 DRβ1 chain and an Epstein-Barr virus (EBV) glycoprotein share a hexapeptide.

Todd et al., *Nature*, 329:599–604 (Oct. 15, 1987) discusses the contribution of the HLA DQβ gene to susceptibility and resistance to IDDM. The authors conclude that "the structure of the DQ molecule, in particular residue 57 of the β-chain, specifies the autoimmune response against the insulin-producing islet cells."

Many HLA DRβ sequences have been published previously. The sequence AspIleLeuGluAspGluArg was reported by Gregersen et al., *PNAS* (USA), 83:2642–2646 (1986) as part of a study of the diversity of DRβ genes from HLA DR4 haplotypes. No mention was made of an association thereof with diabetes. In addition, J. Gorski and B. Mach, *Nature*, 322:67–70 (1986) reported on HLA-DR polymorphism within a group including the haplotypes DR3, DR5 and DRw6. The nucleotide sequences found in the polymorphic regions at the βI locus were not discussed regarding association with diabetes. The first publication on HLA sequences from diabetics is that by D. Owerbach et al., *Immunogenetics*, 24:41–46 (1986). This paper is based on the study on a HLA-DRβ gene library from one IDDM patient. The analysis of class II polymorphism and disease susceptibility requires the comparison of many sequences derived from patients and HLA-matched controls.

Allelic variation in the class II antigens is restricted to the outer domain encoded by the second exon of the protein. Serologic methods for detecting HLA class II gene polymorphism are not capable of detecting much of the variation detectable by DNA methods.

Allelic variations may be detected independently of restriction site polymorphism by using sequence-specific synthetic oligonucleotide probes. Conner et al., *PNAS (USA)*, 80:278 (1983). This technique has been applied to study the polymorphism of HLA DR-β using Southern blotting. Angelini et al., *PNAS* (USA), 83:4489–4493 (1986).

A further refinement of the technique using sequence-specific oligonucleotide probes involves amplifying the nucleic acid sample being analyzed using selected primers, four nucleotide triphosphates, and an appropriate enzyme such as DNA polymerase, followed by detecting the nucleotide variation in sequence using the probes in a dot blot format, as described in now abandoned Ser. No. 899,344, supra, and in now abandoned Ser. No. 839,331 filed Mar. 13, 1986. A temperature cycling process wherein a thermostable enzyme is added only once in the amplification process is described in now abandoned Ser. No. 899,513 and Ser. No. 063,647 now U.S. Pat. No. 4,965,188, filed respectively Aug. 22, 1986 and Jun. 17, 1987, both entitled "Process for Amplifying, Detecting, and/or Cloning Nucleic Acid Sequences Using a Thermostable Enzyme." Now abandoned Ser. No. 899,241 and U.S. Pat. No. 4,889,818, filed respectively Aug. 22, 1986 and Jun. 17, 1987, both entitled "Purified Thermostable Enzyme" disclose and claim thermostable enzymes, purified or recombinant, which can be used in said amplification process.

There is a need in the art for subdivision of the serologic markers HLA DR3, DR4 and DRw6 to obtain more informative and more precisely defined markers for susceptibility to the autoimmune diseases IDDM and PV. Further, there is a need in the art to identify susceptibility conferring haplotypes which are neither DR3, DR4 nor DRw6.

Previously, the distinction between the IDDM associated DQβ variants, DQw3.1 and DQw3.2, of the DR4 haplotype has been made by RFLP or by the use of antibodies. This invention in one aspect relates to methods to identify such DQβ variants.

SUMMARY OF THE INVENTION

Accordingly, the present invention provides a marker DR beta-I DNA sequence from the HLA class II beta genes associated with insulin-dependent diabetes mellitus (IDDM) and with IDDM and with DR4-associated susceptibility to *Pemphigus vulgaris* (PV).

Specifically, in one aspect, the present invention provides a marker DR beta-I DNA sequence associated with IDDM and with DR4-associated susceptibility to *Pemphigus vulgaris* which is GACATCCTGGAAGACGAGCGG, or the DNA strand complementary thereto. Further, the invention provides for the amino acid sequence Asp Ile Leu Glu Asp Glu Arg which is encoded by said DNA sequence.

The present invention also provides for marker DR beta-I DNA sequences associated with DR4, Dw4-associated susceptibility to IDDM wherein one such sequence is GGAGCAGAAGCGGGCCGCG, or the DNA strand complementary thereto. Further, the invention concerns amino acid sequences encoded by said marker DR beta-I DNA sequences associated with DR4, Dw4-associated susceptibility to IDDM and antibodies to said amino acid sequences.

The invention further provides for marker DQβ DNA sequences from the HLA class II beta genes associated with DRw6-associated susceptibility to *Pemphigus vulgaris*. Specifically, such DQβ DNA sequences comprise one or more nucleotide sequences from the second exon of the unique DQβ1.3 allele from about codon 20 to about codon 80. Further, the invention concerns amino acid sequences encoded by such DQB1.3 DNA sequences and antibodies to said amino acid sequences.

In another aspect, the invention provides for a marker DR3 beta-III DNA sequence from the HLA class II beta genes associated with insulin-dependent diabetes mellitus selected from the group consisting of:
  (a) GAGCTGCGTAAGTCTGAG,
  (b) GAGGAGTTCCTGCGCTTC, and
  (c) CCTGTCGCCGAGTCCTGG,
or the DNA strands which are complementary thereto.

In still another aspect, the invention provides an amino acid sequence from HLA class II beta region of the human genome associated with insulin-dependent diabetes mellitus which forms a peptide selected from the group consisting of:
  (a) Glu Leu Arg Lys Ser Glu,
  (b) Glu Glu Phe Leu Arg Phe, and
  (c) Pro Val Ala Glu Ser Trp.

In another aspect, the invention provides a marker DNA sequence from the HLA DQ-beta allele associated with susceptibility to insulin-dependent diabetes mellitus (IDDM), wherein said sequence can be used to detect either directly or indirectly the identity of the codon at position 57 of the DQ-beta protein sequence and marker DNA sequences wherein said codon at position 57 is selected from the group consisting of codons for alanine, valine and aspartate. Said marker DNA sequence is preferably selected from the group consisting of:
  (a) GGGCCGCCTGCCGCC,
  (b) GGGCTGCCTGCCGCC,
  (c) GGGCGGCCTGTTGCC,
  (d) GGGCCGCCTGACGCC, and
  (e) GGGCGGCCTGATGCC,
or the DNA strands which are complementary thereto.

This invention further relates to oligonucleotide probes specific for the 1.5 kb (DQβ3.2) variant and for the 1.8 kb (DQβ3.1) variant DQβ subdivisions of the DR4 haplotype. Specifically, such an oligonucleotide probe specific for the 1.5 kb (DQβ3.2) varient is designated GH74, is a 19-mer and has the sequence: CCGCTGGGGCCGCCTGCCG.

An oligonucleotide probe, designated GH92 specific for the 1.8 (DQβ3.1) RFLP is also a 19-mer and has the following sequence: CGTGGAGGTGTACCGGGCG. Under appropriate hybridization and washing conditions, these oligonucleotides, labeled, for example, with $^{32}p$ by kinasing, or with non-radioisotopic molecule reporters, such as biotin or an enzyme as, for example, horseradish peroxidase, specifically identify the DQβ3.2 and DQβ3.1 variants. This invention further relates to the diagnostic use of such probes.

Further, the invention provides for marker DNA sequences wherein said DNA sequences are used to detect indirectly a second DNA sequence comprising the codon at position 57 wherein said $codon_{57}$ is selected from the group consisting of codons for alanine, valine and aspartate. Said marker DNA sequences used to detect indirectly said second DNA seqence, are preferably selected from the group consisting of:
  (a) GTGGGGGTGTATCGGGCG,
  (b) GTGGGGGAGTTCCGGGCG,
  (c) GTGGAGGTGTACCGGGCG, and
  (d) GTGGGGGTGTACCGGGCA,
or the DNA strands which are complementary thereto.

Further, the invention provides for allele-specific oligonucleotide (ASO) probes that can be used to detect indirectly the identity of codon 57 in the DQβ locus wherein such probes are preferably selected from the group consisting of:
  (1) a 19-mer designated GH61 from the DQ-beta-B region of the DR3 haplotype having the nucleotide sequence: CGGCAGGCAGCCCCAGCAG;
  (2) a 19-mer designated GH66 from the DQα region of the DR3 haplotype having the nucleotide sequence: TGTTTGCCTGTTCTCAGAC; and
  (3) a 21-mer designated GH70 from the DQ-beta-A region of the DR3 haplotype having the nucleotide sequence: GATGCTTCTGCTCACAAGACG.

The invention also relates to a process for detecting the presence or absence of sequences associated with susceptibility to insulin-dependent diabetes mellitus and/or *Pemphigus vulgaris* in a DNA sample comprising:
  (a) treating the sample to expose the DNA therein to hybridization;
  (b) affixing the treated sample to a membrane;
  (c) treating the membrane under hybridization conditions with a labeled sequence-specific oligonucleotide probe capable of hybridizing with one or more of the DNA sequences selected from the group consisting of:
    (1) GAGCTGCGTAAGTCTGAG,
    (2) GAGGAGTTCCTGCGCTTC,
    (3) CCTGTCGCCGAGTCCTGG,
    (4) GACATCCTGGAAGACGAGCGG,
    (5) GGGCCGCCTGCCGCC,
    (6) GGGCTGCCTGCCGCC, and
    (7) GGGCGGCCTGTTGCC,
  or with the DNA strands complementary thereto; and
  (d) detecting whether the probe has hybridized to any DNA in the sample.

Still further, the invention concerns an antibody that binds to one or more of the amino acid sequences selected from the group consisting of:
  (a) Glu Leu Arg Lys Ser Glu,
  (b) Glu Glu Phe Leu Arg Phe,
  (c) Pro Val Ala Glu Ser Trp, and
  (d) Asp Ile Leu Glu Asp Glu Arg.

The invention also concerns an antibody that binds to a peptide segment containing an epitope comprising an amino acid residue corresponding to position 57 of a DQ-beta protein, wherein said antibody may have cross-reactivity with a homologous peptide sequence encoded by a human persistent viral pathogen, and wherein said amino acid residue is selected from the group consisting of alanine and valine. Said antibody preferably binds to a peptide selected from the group consisting of:
  (a) Gly Pro Pro Ala Ala,
  (b) Gly Leu Pro Ala Ala, and
  (c) Gly Arg Pro Val Ala.
Further, said viral pathogen is preferably selected from the group of viruses consisting of Epstein-Barr virus, rubella virus, Coxsackie virus, cytomegalovirus, and reovirus.

Still further, the invention relates to a process for detecting the presence or absence of sequences associated with susceptibility to insulin-dependent diabetes mellitus in a protein sample comprising:

(a) incubating the sample in the presence of one or more of the antibodies that bind to a peptide selected from the group consisting of:

Gly Pro Pro Ala Ala,

Gly Leu Pro Ala Ala, or

Gly Arg Pro Val Ala;

wherein said antibodies are labeled with a detectable moiety; and (b) detecting the moiety. The antibodies can be polyclonal or monoclonal. Said process for detecting IDDM associated sequences includes those processes wherein before, during, or after incubating with the labeled antibody, the sample is incubated in the presence of a monoclonal antibody that is immobilized to a solid support and binds to one or more of the amino acid sequences selected from the group consisting of:

(a) Gly Pro Pro Ala Ala, (b) Gly Leu Pro Ala Ala, and (c) Gly Arg Pro Val Ala.

The invention further concerns a process for identifying haplotypes associated with susceptibility to insulin-dependent diabetes mellitus in a serum sample comprising:

(a) incubating the sample in the presence of one or more of the peptides selected from the group consisting of Gly Pro Pro Ala Ala, Gly Leu Pro Ala Ala, and Gly Arg Pro Val Ala;

(b) detecting the presence of immune complexes formed between said peptide and an antibody present in said serum sample; and (c) determining from the results of step (b) whether a susceptible haplotype is present. The peptides used in said process can be labeled with a detectable moiety, and the detection can be by enzyme reaction, fluorescence or luminescence emission.

The invention further concerns the prophylactic and therapeutic use of the above-referenced antibodies and peptides.

In another aspect, the invention provides a kit for detecting the presence or absence of sequences associated with susceptibility to insulin-dependent diabetes mellitus or *Pemphigus vulgaris* in a DNA sample, which kit comprises, in packaged form, a multicontainer unit having one container for each labeled sequence-specific DNA probe capable of hybridizing with one or more of the DNA sequences identified above or with the DNA strands complementary thereto.

In a final aspect, the invention provides a kit for detecting the presence or absence of amino acid sequences associated with susceptibility to insulin-dependent diabetes mellitus or to *Pemphigus vulgaris* in a protein sample, which kit comprises, in packaged form, a multicontainer unit having a container for each antibody labeled with a detectable moiety that binds to one or more of the amino acid sequences identified above.

As mentioned above, genetic susceptibility to IDDM has been correlated in both family and population studies with the presence of the serologic markers HLA DR3 and DR4. The highest risk for IDDil is associated with HLA DR3,4 heterozygotes, suggesting that the susceptible alleles associated with these two DR types may be different and that two doses may be required for high risk to IDDM. Previous restriction fragment length polymorphism analysis has subdivided DR3 and DR4 into two subsets each.

Similarly, as mentioned above, genetic susceptibility to PV has been correlated with the presence of the serologic markers HLA, DR4 and DRw6. Previous restriction fragment length polymorphism has subdivided the DR4 and DRw6 haplotypes.

Molecular analyses of the HLA genes herein has resulted in further subdivision of the HLA DR3, DR4 and DRw6 serological types and in the generation of novel, more informative, and more precisely defined genetic markers for susceptibility to IDDM and PV. The molecular techniques herein reveal not only that the number of class II loci is unexpectedly large, but also that the allelic variation at these loci is greater than the polymorphic series defined by serological typing and can be more precisely localized.

DESCRIPTION OF FIGURES

FIG. 1 illustrates the sequence of the DRS fragment PCR (polymerase chain reaction) amplified according to Example III. The sequences of the PCR primers are shown by long arrows, which also indicate the direction of extension by the polymerase. The broken lines show the BamHI and PstI recognition sequences used to generate restriction sites for cloning. The start of the second exon sequence is shown by the short arrow and the region of the fragment corresponding to the Dw10 sequence specific oligonucleotide GH78 is shown by the bracketed segment. Digestion with BamHI and PstI produces a 248 bp fragment for cloning. The sequence shown here represents a prototype DRB1 allele from the DR4 Dw10 haplotype.

FIG. 2 illustrates the amino acid sequences for the HLA DRβ second exon from three *Pemphigus vulgaris* (PV) (see Example III) and from DRβ prototypes [Gregerson et al., *PNAS* (USA), 83:2642–2646 (1986)] using the standard one-letter amino acid code (see Table VIII, infra). The entire amino acid sequence of the DRβ1 allele from a DR4 Dw4 haplotype is shown whereas the other sequences are aligned with it using a dash to indicate homology and letters to indicate polymorphic amino acids. The DR type (and the Dw type where appropriate) and the DRβ locus assignment are shown at the right end of each sequence. "I" refers to the DRβ1 locus, "III" for the DRβIII locus which encodes the DRw52 specificity, and "IV" for the DRβIV locus, which encodes the DRw53 specificity. The fragments obtained by PCR cloning are smaller than the prototype sequences, which are derived from cDNA clones.

FIGS. 4A–4B illustrate the alignment of HLA-DQβ protein sequences. DNA sequences of DQβ alleles were translated to the standard one-letter amino acid code (Table VIII, infra) and aligned to show patterns of homology. A dash indicates homology with the equivalent amino acid in the prototypic DQβ (DR4) allele. A blank indicates that the sequence was not determined. Location of the PCR amplification primers are shown on the bottom. Note that the PCR amplification procedure only determines the sequence between the oligonucleotide primers [Scharf et al., *Science*, 233:1076–1078 (1986)]. The source of each sequence is designated on the left of each line, and its DR serologic type is shown on the right. An asterisk after the DR type indicates that the allele was determined from a patient with IDDM.

The Hu129 sequence was determined from a PV patient. On the far right is the designation of the allele, corresponding when possible with the DQw typing of the haplotype. The DCB4 sequence was from Larhammar et al., *PNAS* (USA), 80:7313–7317 (1983); CMCC and MMCC are from Horn et al., DQB37 from Michelsen et al., *J. Clin. Invest.*, 79:1144–1152 (1987); KT3 from Gregersen et al., *PNAS* (USA), 83:2642–2646 (1986); WT49 from Boss et al., *PNAS* (USA), 81:5199–5203 (1984); BURK from Karr et al., *J. Immunol.*, 137:2886–2890 (1986); LG2 from Bull et al., *PNAS* (USA), 82:3405–3409 (1985); DQBS4 and DQBS5 from Tsukamoto et al., *Immunogenetics*, 25:343–346 (1987); AZH, BGE, and PGF from Lee et al., *Immunogenetics*, 26:85–91 1987); and the related DXβ sequence was from Okada et al., *PNAS* (USA), 82:3410–3414 (1985). The PCR sequence illustrated for PGF matched the published cDNA. The DQB alleles reported for the two IDDM patients, DC and JR, were the only DQB3.1 alleles observed in 34 DR4 patients.

Figure 4B:
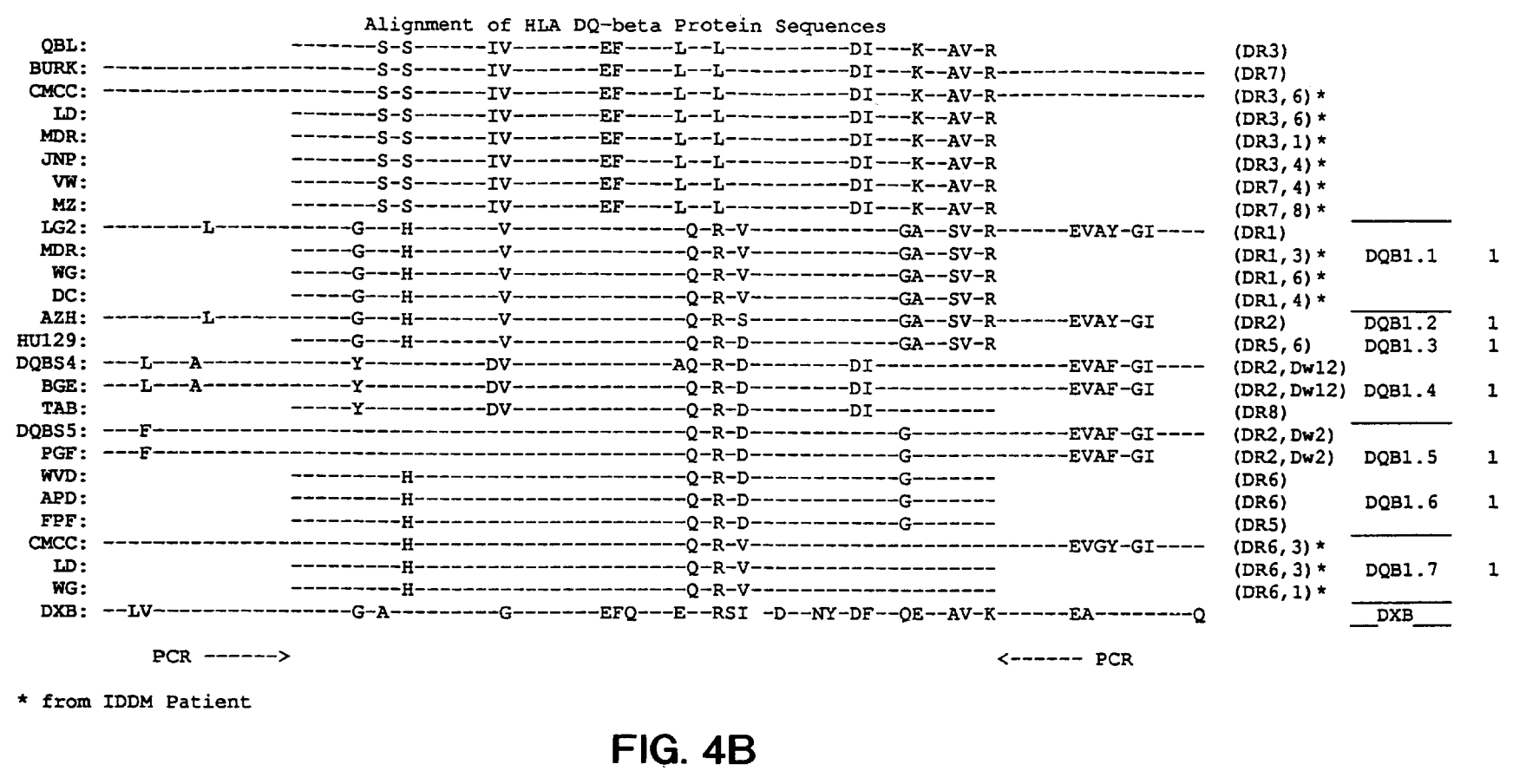
Figure 5A:
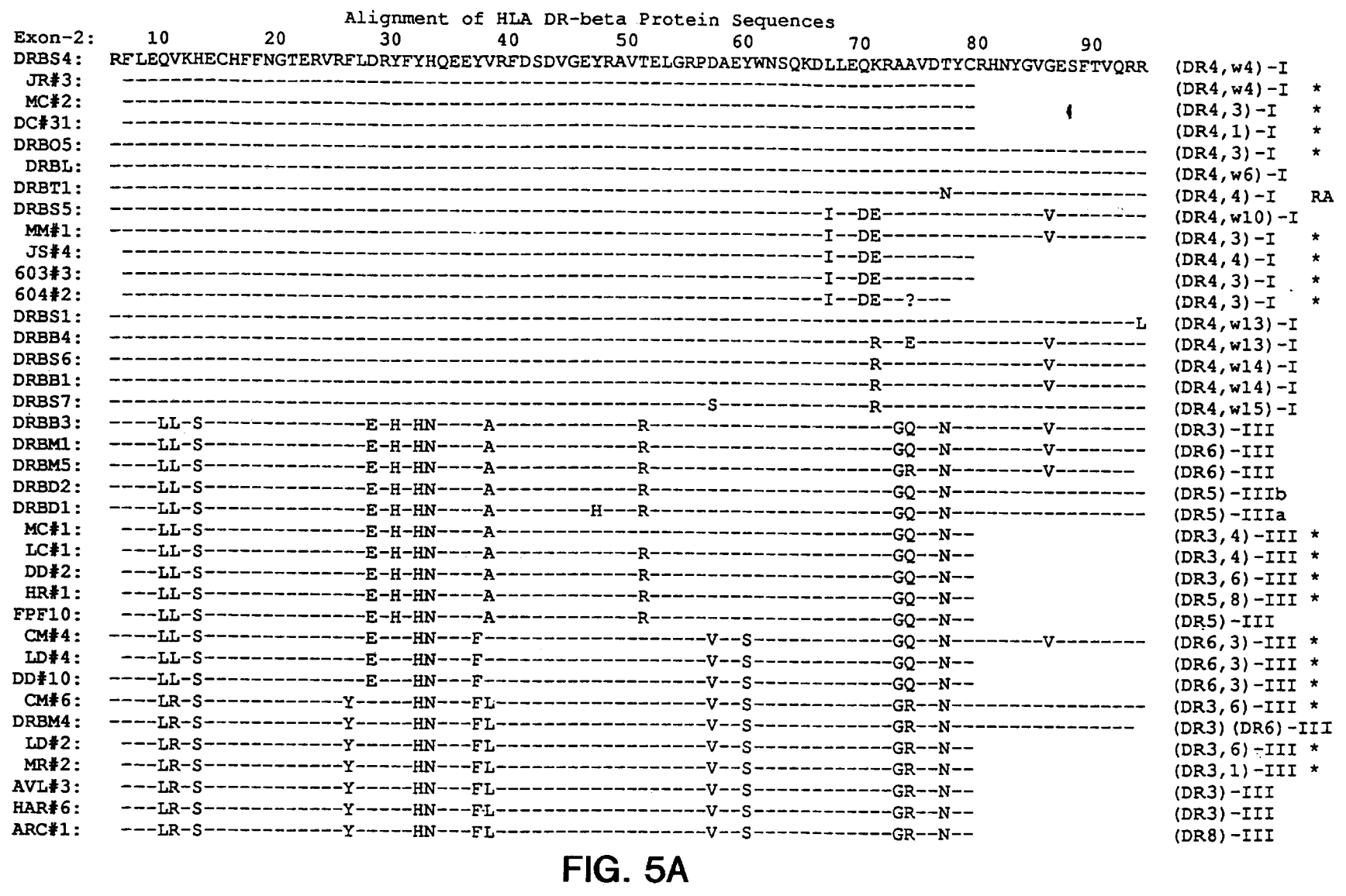
Figure 5C:

FIGS. 5A–5C illustrate the alignment of HLA-DR-beta protein sequences. DNA sequences of the DRβ alleles were translated to the standard one-letter amino acid code (Table VIII, infra) and aligned to show patterns of homology. The conventions used are the same as explained in the description for FIG. 4, supra. See also Example I, infra.

DESCRIPTION OF THE PREFERRED EMBODIMENTS

Allelic sequence variations reported herein have been compared with conventional HLA classifications, and a new nomenclature based on the correspondence between current DQw serological specificities and sequence patterns is used. Specifically, the DNA-defined types DQB1, DQB2 and DQB3 designate sequences derived from the serologically defined DQw1, DQw2 and DQw3 haplotypes respectively, whereas DQB4 designates those sequences derived from DQ (blank) haplotypes, which are apparently homogeneous. Employed In such nomenclature is the convention of using Greek letters for the genetic loci and for the protein products (e.g., the DQβ locus encoding the DQβ chain) and of using Roman capital letters followed by a number to designate the specific allelic sequence variants (e.g., the DQB2 allele). Sequence variants which subdivide such types are designated by a subtype number (e.g., DQB1.2 or DQA1.3).

However, the designation of DQα allelic variants do not always correspond to the DQw specificity; for example, the DQA4 type is associated with both the DQw2 and DQw3 haplotypes. That is because the DQw2 and DQw3 specificities appear to be determined by polymorphic epitopes on the β-chain, independently of allelic variation on the α-chain.

"Positively associated" with an autoimmune disease is a term used herein to mean that the frequency of a marker is increased in patients with the disease relative to controls (individuals without the disease). The converse meaning applies to the term "negatively associated" with an autoimmune disease, that is, the frequency of the marker is decreased in patients relative to controls.

The terms "oligonucleotide" as used herein is defined as a molecule comprised of two or more deoxyribonucleotides or ribonucleotides, preferably more than three. Its exact size will depend on many factors, which in turn depend on the ultimate function or use of the oligonucleotide. The oligonucleotide may be derived synthetically or by cloning.

The term "sequence-specific oligonucleotides" (SSOs) refers to oligonucleotides which will hybridize to one of the specific DNA sequences identified herein, which are regions of the loci where allelic variations may occur. Such oligonucleotides have sequences spanning one or more of the DNA regions being detected and are specific for one or more of the regions being detected. One sequence-specific oligonucleotide is employed for each sequence to be detected, as described further hereinbelow.

The term "monoclonal antibodies" as used herein refers to an immunoglobulin composition produced by a clonal population (or clone) derived through mitosis from a single antibody-producing cell. Unless otherwise indicated, the term is not intended to be limited to antibodies of any particular mammalian species or isotype or to antibodies prepared in any given manner. The term is intended to include whole antibody molecules as well as antigen-binding fragments (e.g., Fab, F(ab')$_2$, Fc, Fc').

An "antibody-producing cell line" is a clonal population or clone derived through mitosis of a single antibody-producing cell capable of stable growth in vitro for many generations. The term. "cell line" refers to individual cells, harvested cells, and cultures containing cells so long as they are derived from cells of the cell line referred to. Preferably the cell lines remain viable for at least about six months and maintain the ability to produce the specified monoclonal antibody through at least about 50 passages.

As used herein, the term "incubation" means contacting antibodies and antigens under conditions (e.g., proper pH, temperature, time, medium, etc.) that allow for the formation of antigen/antibody complexes also referred to as immune complexes. Also as used herein, "separating" refers to any method, usually washing, of separating a composition from a test support or immobilized antibody, such that any unbound antigen or antibody in the composition are removed and any immune complexes on the support remain intact. The selection of the appropriate incubation and separation techniques is within the skill of the art.

HLA class II DR-beta genes have been isolated from HLA-typed IDDM patients and HLA-matched controls and have been sequenced, resulting in regions of specific nucleotide and amino acid sequence which occur in various combinations and which are associated with IDDM. These specific sequences can be used in DNA or protein diagnostic procedures to determine genetic susceptibility to IDDM.

Four variant DR-beta sequences A-D found to be associated with IDDM are shown below. In each case, DNA sequences seen in the diabetic genomes produce an alteration in one to three amino acid residues (underlined) of the DR-beta protein. The amino acids normally found in these positions are shown in parentheses. Sequences A-C are from the DRβIII region whereas sequence D is from the DRβI region. Sequence D encompasses the "I-DE" (isoleucine, aspartic acid, glutamic acid at positions 68, 71 and 72) epitope discussed infra.

```
A.    . . . GluLeuArgLysSerGlu . . .
      . . . GAGCTGCGTAAGTCTGAG . . .
      . . . CTCGACGCATTCAGACTC . . .
          (Val,Ser,Leu,Pro,Asp,Ala)

B.    . . . GluGluPheLeuArgPhe . . .
      . . . GAGGAGTTCCTGCGCTTC . . .
      . . . CTCCTCAAGGACGCGAAG . . .
          (Tyr,Asn,Ser,Asp)

C.    . . . ProValAlaGluSerTrp . . .
      . . . CCTGTCGCCGAGTCCTGG . . .
      . . . CCGCAGCGGCTCAGGACC . . .
          (Asp,Ser)   (Tyr)
```

-continued

```
D.  . . . AspIleLeuGluAspGluArg . . .
    . . . GACATCCTGGAAGACGAGCGG . . .
    . . . CTGTAGGACCTTCTGCTCGCC . . .
         (Leu,Phe)  (Gln,Arg,Glu)  (Lys,Arg,Ala)
```

Table I below shows the IDDM susceptibility and DR-beta variation within the DR3 and DR4 haplotypes. Table II shows the correlation between the haplotypes and sequences A-D identified above. Sequences A, B and C are correlated with B8, DR3 vs. non B8, DR3 haplotypes.

TABLE I

|  | DR3 | DR4 |
|---|---|---|
| DRβ1 | Not variable | Variable (5) |
| DRβ3 | Variable (2) | Not variable |

TABLE II

| Type | Gene | Sequence | | | |
|---|---|---|---|---|---|
|  |  | A | B | C | D |
| DR4 | beta-I | − | − | − | + |
| DR6 | beta-I | − | − | − | + |
| DR6 | beta-III | − | + | + | − |
| DR3 | beta-III | + | + | + | − |

TABLE II-continued

| Type | Gene | Sequence | | | |
|---|---|---|---|---|---|
|  |  | A | B | C | D |
| DR3 | beta-III | + | + | − | + |
| DR3 | beta-III | − | + | − | − |

Now abandoned U.S. Ser. No. 899,344 filed Aug. 22, 1986 entitled "Process for Detecting Specific Nucleotide Variations and Genetic Polymorphisms Present in Nucleic Acids," discloses the general method of analyzing allelic sequence variation by using allele-specific oligonucleotide (ASO) probes to hybridize to PCR amplified DNA in a dot blot format. That application, incorporated herein by reference and for which priority is claimed herein, lists some specific DNA and protein translation sequences derived from PCR cloning of several HLA class II (e.g., DRβ, DQa, and DQb) genes from a variety of HLA-typed individuals, either IDDM patients or controls. Some of such DNA sequences, identified by PCR and detectable by PCR/dot blot/ASO analysis, can function as useful markers for disease susceptibility or differential diagnosis. One such informative set of DNA and translation sequences are the DQβ sequences shown below in Tables III and IV (Tables IV and V in U.S. Ser. No. 899,344, abandoned), which respectively list the DNA and amino acid translation sequences for a number of allelic variants in the HLA-DQβ region. The designations DR4, DR4' and DR4' therein are equivalent respectively to the terms DQB3.2, DQB3.1 and DQB4 (blank).

TABLE III

```
HLA-DQβ (segment A):

20              25              30
         GlyThrGluArgValArgGlyValThrArgHisIleTyr
         GGGACGGAGCGCGTGCGGGGTGTGACCAGACACATCTAT  DR1
         ------------------TTA---------T--------  DR4'
         ------------------TCT---------T--------  DR2,4
         ------------------TCT---A--------------  DR6
         -----C-----------------------T--------  DR8
         -----C----T------------------T--------  DR4"
         -----A------------TCT-----G----AG------ DR3,7
    DXB: -----A------------C------G-----T--------

HLA-DQβ (segments B and D):

|  segment D  |              | segment B |
         |      45     |   50         |    55  57 |   60
         ValGlyValTyrArgAlaValThrProGlnGlyArgProValAlaGluTyrTrpAsn
         GTGGGGGTGTACCGGGCAGTGACGCCGCAGGGGCGGCCTGTTGCCGAGTACTGGAAC  DR1
         --------------C--G---------------------A----------------  DR2
         -----------------G--------------------------------------  DR6
         -----------T-----G----------T-----C-----CC--------------  DR4
         ----A------------G----------T-----C-----AC--------------  DR4'
         -----------T-----G----------T--------T--AC-------------T  DR8
         --------A--T------G-------T--T-----T-----CC--------------  DR3,7
    DXB: --T----A--T--A---G-----CGA--T-------AGCA-C-AG--C---------

HLA-DQβ (segment C):

66              70              75
         GluValLeuGluGlyAlaArgAlaSerValAspArgVal
         GAAGTCCTGGAGGGGGCCCGGGCGTCGGTGGACAGGGTG  DR1
         ----------------A--------GA-T------C----  DR2
         ------------A--A--------GA-T------C----  DR4,6 and DR4'
         --CA---------A--A-----------------CC---  DR8
         --CA---------A--AAA------G-------------  DR3,7
         --CT--T-----CA--AG-----CG---------A----
```

TABLE IV

Alignment of HLA-DQβ Protein Sequence

```
Exon-2:         20                  40                  60                  80
DCBPG:  DFVVQFKGMCYFTNGTERVRLVTRYIYNREEYARFDSDVGVYRAVTPLGPPAAEYWNSQKEVLERTRAELDTVCRHNYQLELRTTLQRR    DQB3.2(4)
JoanP:  ----------------------------------------------------------------------------------------    DQB3.2(4,3)
MMCC4:  ----------------------------------------------------------------------------------------    DQB3.2(4)
NIN:    -------------------Y--------------E-----------------------------------------------------    DQB3.1(4')
ARC:    -----------------------------------------G--------------RLD------DI--ED--SV-------------    (DR8)
DO96:   -----------------------------------------G--------------RLD------DI--ED--SV-------------    (DR8,7)
DQBS3:  ---F-------------L--G----------------------------------------RLD------DI--ED--SV-------------    DQB4(*)(4")
DCBP1:  ---------------------------------S-S-------VV-----EF------L--L-----------DI--K--AV--R------    (DR3,6)
DO96:   ---------------------------------S-S-------IV-----EF------L--L-----------DI--K--AV--R------    (DR7,8)
CMCC3:  ---------------------------------S-S-------IV-----EF------L--L-----------DI--K--AV--R------    (DR3)
DCBS1:  ---------------------------------S-S-------V------EF------L--L-----------DI--K--AV--R------    (DR3)
DQBC:   ---------L---------------------------G-----V-------------Q-R--V----------GA--SV--R----EVAY--GI---    (DR1)
DCBP2:  ---------L---------------------------G-----V-------------Q-R--V----------GA--SV--R----EVAY--GI---    (DR1,6)
TAB:    ---------------------------------------Y--DV-------------Q-R--D----------DI-----------------    (DR8)
DQBH:   ---F----------------------------------------------------Q-R--D----------G-----------EVAF--GI---    (DR2)
PGF:    ---------------------------------------------------------Q-R--D----------G-----------EVAY--GI---    (DR2)
CMCC6:  -------------------------H----------------------------Q-R--V----------G-----------EVGY--GI---    (DR6)
DXB:    --LV---------------------------G-A----G----EFQ---E--RSI--D--NY--DF--QE--AV--K---EA-----Q        
                |_____A_____|        |__D__|  |__B__|                                          |___C___|
```

\* = blank

Specifically, sequences for two variants of the serologically defined DR4 haplotype listed as DR4 (DQB3.2) and DR4' (DQB3.1) In Tables III and IV are particularly informative. This DQβ subdivision of the DR4 haplotype was correlated with a DQβ RsaI RFLP in which one DR4 variant had a RsaI fragment of 1.8 kb and another had a RsaI fragment of 1.5 kb (Arnheim et al., supra). Among DR4 individuals the 1.5 kb variant (DR4) was found to be positively associated with IDDM whereas the 1.8 kb fragment (DR4') was found to be negatively associated with IDDM as indicated by Table A below.

TABLE A

|  | IDDM | Controls | Relative Risk |
|---|---|---|---|
| DR4 | 34/46 | 15/57 | 7.9 |
| DR4 (1.5 kb; DQB3.2) | 32/46 | 10/57 | 10.8 |
| DR4' (1.8 kb; DQB3.1) | 2/46 | 5/57 | 0.47 |

$$\text{Relative Risk} = \frac{(\text{\# patients with marker})(\text{\# controls without marker})}{(\text{\# patients without marker})(\text{\# controls with marker})}$$

The DR4 (DQB3.2) and DR4' (DQB3.1) sequences differ by five nucleotide substitutions which result in three different amino acid changes. Two of the changes (Gly to Glu at codon 45 and Ala to Asp at codon 57) are non-conservative and have major charge differences. The presence of a valine or alanine at codon 57 relative to aspartic acid is considered to be positively associated with susceptibility to IDDM.

One of the most significant differences between the DQβ alleles seen in the DR4 haplotypes, designated DQB3.1 and DQB3.2, is found at position 57. (The numbering used herein corresponds to the amino acids in the processed protein.) The allele in the DQB3.1 haplotype, which is not associated with IDDM susceptibility, has an aspartate residue at position 57, whereas the allele in the DQB3.2 haplotype, which is strongly associated with IDDM susceptibility, has an alanine residue at position 57. Further, the DR3 haplotype which is positively associated with IDDM, has an alanine at position 57. The DR2 haplotype, negatively associated with IDDM, also has an aspartate residue at position 57.

Also, it was found that of two DQβ alleles in the DRw6 haplotypes, the allele positively associated with IDDM has a valine at position 57, whereas the allele negatively associated with IDDM has again an aspartate at position 57. Still further, it was found that the DR1 haplotype which is moderately associated with IDDM has a valine at position 57 in the DQβ locus.

Based on such observations, it was determined that the pattern of amino acid variation at position 57 parallels the pattern of susceptibility to IDDM. Alleles containing alanine (hydrophobic residue) at position 57 are most highly associated with IDDM, alleles containing valine (hydrophobic residue) at position 57 being moderately associated with IDDM, and alleles containing aspartate (charged residue) at 57 being negatively associated with IDDM.

A major exception to this pattern is the DQB2 allele of the DR7 haplotype which has an alanine at position 57 as does the DR3 haplotype but unlike DR3, is not associated with IDDM susceptibility.

Such a pattern extends to other genes also. For example, an allele of the DRβ-III gene within the DR3 haplotype, correlated with increased IDDM susceptibility, has a valine at position 57, whereas most of the other DRβ alleles have aspartate at position 57. Thus, it was determined that the hydrophobic valine at position 57 of the DRβ-III allele is associated with IDDM susceptibility as well as the hydrophobic alanine in the DQβ allele.

Table V below summarizes the sequences found around position 57 in a number of genes. An asterisk in Table V indicates those haplotypes associated with greatest IDDM susceptibility.

TABLE V

Variation in MHC class II β Proteins at Position 57

```
DQβ                      Position 57
                              ↓
       DR2, DR6.1       ... GRPDAEY ...
       DR8              ... --L---- ...
       DR4.1 (aka       ... -P----- ...
         DQw3.1)
       DR4.2 (aka       ... -P-A--- ... *
         DQw3.2)
       DR3, DR7         ... -L-A--- ... *
       DR1, DR6.2       ... ---V--- ... *

DRβ-III:
       DR3.1, DR6.1,    ... GRPDAEY ...
         DR5
       DR3.2, DR6.2,    ... ---V--S ... *
         DR8

DRβ-I:
       (consensus)      ... GRPDAEY ...
       Dw15, DR8        ... ---S--- ...
       DR7, DR9         ... ---V--S ...
       DR6.2            ... ---A-DD ...
       DR5              ... ----E-- ...

I-Aβ:
       d, k, b, u, s, q ... GRPDAEY ...
       f                ... --S---- ...
       NOD              ... --HS--- ... * (IDDM -
                                            suscep-
                                            tible
                                            NOD
                                            mouse)

I-Eβ:                    Position 57
                              ↓
                        ... GRPDAEN ...

DPβ:
                        ... GRPAAEY ...
                        ... ---DE-- ...
                        ... ----E-- ...
                        ... ---E--- ...
                        ... ---DED- ...
```

Table V indicates that three amino acid sequences encoded by DQβ alleles are associated with IDDM susceptibility. These sequences and the nucleotide sequences encoding them are listed in Table VI below. Also listed therein are the nucleotide and amino acid translation sequences about position 57 indicative of alleles negatively associated with IDDM susceptibility. Codon 57 is underlined therein.

TABLE VI

| Allele | Sequence | | | | | IDDM Association |
|---|---|---|---|---|---|---|
| DQ-beta (DR4): (DRw3.2) | Gly GGG | Pro CCG | Pro CCT | Ala <u>GCC</u> | Ala GCC | ++ |
| DQ-beta (DR3): | Gly GGG | Leu CTG | Pro CCT | Ala <u>GCC</u> | Ala GCC | ++ |

TABLE VI-continued

| Allele | Sequence | IDDM Association |
|---|---|---|
| DQ-beta (DR1,6): | Gly Arg Pro Val Ala<br>GGG CGG CCT GTT GCC | + |
| DQ-beta (DR4):<br>(DQw3.1) | Gly Pro Pro Asp Ala<br>GGG CCG CCT GAC GCC | − |
| DQ-beta (DR2): | Gly Arg Pro Asp Ala<br>GGG CGG CCT GAT GCC | − |

The sequences in Table VI are considered to be marker DNA sequences from HLA DQβ alleles that can be used to directly detect the identity of the codon at position 57 that encodes for alanine, valine or aspartate.

Indirect ASO Analysis

Although sequences around position 57 in the DQβ protein are those most positively associated with IDDM susceptibility, marker sequences directly hybridizing thereto may not be optimal for inclusion in oligonucleotide probes. Since the DQβ alleles differ in other areas and are closely associated with other loci, such as DQα alleles, the identity of the amino acid at position 57 of the DQβ alleles can be determined by the use of one or more oligonucleotide probes that hybridize to other regions of the DQβ, DQα or other HLA D regions. Further, such identification can be achieved by using one or more probes wherein one probe hybridizes to the region around position 57 and wherein one or more other probes hybridize to another HLA region in linkage disequilibrium therewith.

For example, the DR3 haplotype is strongly associated with IDDM susceptibility and contains an alanine at position 57 in DQβ. Although this region can be detected directly with an ASO probe, such as GH74 (see Summary, supra), the G/C-rich nature of that segment of DQβ leads to less than optimal probes because of the base mismatching potential associated therewith. The GH70 ASO probe (see Summary supra), however, is specific for a region about 90 bp upstream, from codon 57 in an area that is not as G/C-rich and thus avoids the base mismatching problem of a direct probe for the position 57 segment. Thus, the binding of the GH70 ASO probe identifies indirectly the DQβ allele wherein codon 57 encodes alanine.

Probes even farther away from the DQβ codon 57 position can also be used. For example, the GH66 ASO probe (see Summary supra) is specific for the DR3 allele of the DQα locus, located about 12 kbp away from DQβ. However, as the DR3 allele of DQα locus has been shown to be consistently linked with the DR3 allele of the DQβ locus, the binding of the GH66 probe identifies not only the DQα DR3 allele, but also the DQβ DR3 allele. The use of the DQα locus also provides for discrimination between the IDDM susceptible DR3 haplotype and the less susceptible DR7 haplotype.

Other Autoimmune Diseases

Susceptibility to other autoimmune diseases may also be related to codon 57 polymorphism. The DRw6 susceptibility to *Pemphigus vulgaris* is associated with a rare DQβ allele (DQB1.3) which differs from the non-susceptible alleles DQB1.2 and DQB1.1 only by a charge variation at position 57 and is correlated with the Dw9 DRw6 subtype. Similarly, a DPβ allele found thus far only in celiac disease patients differs from an allele found in a homozygous typing cell (HTC) by an Ala-Asp substitution at position 57 (Bugawan et al., unpublished). [Celiac disease is a digestive disorder characterized by a malabsorption syndrome affecting both children and adults precipitated by the ingestion of gluten-containing foods; its etiology is unknown but a hereditary factor has been implicated.] Described in Example III is the sequencing of the polymorphic second exon of the DRs1, DRβII and DQβ loci from three PV patients to discern any possible disease association with specific polymorphic class II epitopes. In the DQβ loci, 3 of 4 DR4 haplotypes contained the DQB3.2 allelic sequence variant present on 60–80% of control DR4 haplotypes, and one of the four DR4 haplotypes contained the DQB3.1 allele, present on about 20–40% of control DR4 haplotypes [Erlich, et al., in Schacter et al. (eds): *The Molecular Analysis of Histocompatibility Antigens*, pp. 93–109 (1987); Arnheim et al., *PNAS* (USA), (1985) 82:6970–6974; Kim et al., *PNAS* (USA), (1985) 82:8139–8143]. The two DR5 haplotypes also contained the DQB3.1 allelic sequence variant present on all control DR5 haplotypes. Thus, the distribution of DQβ alleles was essentially the same in patients, and in DR-matched controls. In this small sample, all three patients were DQB3.1/DQB3.2 heterozygotes.

In the DRβI locus, however, a potentially interesting pattern could be discerned. All three PV patients contained a DR4 haplotype with a DRβI allelic sequence variant associated with the MLC-defined subtype, Dw10. In the U.S. population the frequency of the Dw10 subtype among DR4 haplotypes is estimated to be approximately 10% [Hansen et al., *Brit. Med. Bull.* (1987) 43:203–216]. This observation was confirmed using oligonucleotide probes rather than sequence analysis with virtually 100% of DR4 PV patients containing the Dw10 epitope. Since this epitope is associated with the MLC-defined type, Dw10, it is likely to be recognized by the T-cell receptor. These results suggest that for DR4 associated susceptibility the amino acid residues isoleucine, aspartic acid and glutamic acid at positions 68, 71, and 72 of the DR4 DRβI chain play a role in PV autoimmunity. Such residues define an epitope herein identified as the "I-DE" epitope. [See Example III.]

As indicated in Example IV, the same "I-DE" epitope around codon 70 is also present on a subset of DRw6 haplotypes, but said epitope was not shown to be positively associated with PV in such DRw6 haplotypes. As the "I-DE" shared epitope cannot account for the DRw6 susceptibility, further research was performed to find sequences conferring PV susceptibility within the DRw6 haplotype by determining the sequences of the DQβ alleles of two DR5/DRw6 PV patients by methods exemplified in Example III. Both patient DRw6 haplotypes were found to contain a previously unknown DQβ allele, which was designated DQB1.3 (see HU129 sequence of FIG. 4). The DQB1.3 allele differs from the DR1 DQβ allele, DQB1.1 by only a valine to aspartic acid substitution at position 57. Analogously, it differs from the rare DR2 AZH DQβ allele, DQB1.2, by only a serine to aspartic acid substitution at position 57. At the nucleotide level, the DQB1.3 allele is identical in the region around position 57 to the DR2 Dw12 (DQB1.5) allele, DQβ, and to the most common DRw6 DQβ allele DQB1.6.

To determine the frequency of the DQB1.3 allele among PV patient and control DRw6 haplotypes, pairs of sequence-specific oligonucleotide (SSO) probes were used to identify both the DR1-like DQβ framework sequence and the sequence around codon 57. Exemplary SSO probes are as follows:

(1) GH69 a 21-mer which identifies a DR1-like DQβ framework and has the nucleotide sequence GATGT-GTCTGGTCACACCCCG;

(2) GHBO a 19-mer which identifies a DRw6-like framework and has the nucleotide sequence TCTTGTAACCA-GACACATC;

(3) CRX03 a 19-mer which identifies a sequence about codon 57 wherein codon 57 encodes for aspartic acid and has the nucleotide sequence TCGGCGTCAGGCCGC-CCCT; and (4) CRX02 a 19-mer which identifies a sequence around codon 57 wherein codon 57 encodes for valine and has the nucleotide sequence TCGGCAACAGGCCGCCCCT.

Using the above-designated probes, a pattern of hybridization can be used to identify and distinguish specific alleles. The following chart exemplifies the use of such a method wherein a plus sign (+) indicates hybridization of the SSO probe to the target DNA sample.

| Alleles | Probes | | | |
|---|---|---|---|---|
|  | GH69 | GH80 | CRX03 | CRX02 |
| Dw9 1.3 | + |  | + |  |
| 1.1 | + |  |  | + |
| Dw18 1.6 |  | + | + |  |
| Dw19 1.7 |  | + |  | + |

Using this approach, 11 of the 13 DRw6 patient haplotypes (85%) contained the DQB1.3 allele, whereas only one of the 13 control DRw6 haplotypes (8%) contained said allele. [The other two DRw6 patients had DQβ alleles that had the DR1-like framework (identified by GH69) but failed to hybridize with either the CRX03 or the CRX02 probes.]

The findings indicate that the DRw6 associated PV susceptibility could be conferred by the rare DQβ allele DQB1.3 that differs from the common DQβ allele DQB1.1 by only one residue. Such a single charge difference of the polymorphic residue at position 57 of the DQ beta chain associated with the DRw6 associated PV susceptibility correlates with that found for the DR4 and DR3 associated susceptibility for IDDM. However, in the case of PV, it is clear that it is the allele rather than the epitope around position 57 that confers susceptibility because the most common DRw6 DQβ allele that is, DQB1.6, which is not associated with PV, has the same sequence around position 57. Since the DQB1.6 allele differs at other regions of its sequence (see FIG. 4), it is possible to differentiate the DQB1.6 common allele from the rare DQB1.3 allele by the use of pairs of SSO probes, for example, as indicated immediately above, the GH69, GH80, CRX03, and CRX02 probes or ones substantially similar thereto.

The conclusion that the novel DQβ allele accounts for the DRw6 associated susceptibility to PV is consistent with DQβ RFLP analysis of Sfazer et al., supra (1987).

Viral Mimicry and Autoimmune Disease

Although the pattern of DQβ allelic variation clearly implicates position 57 in autoimmune predisposition, this region does not appear to be the only class II epitope within susceptibility conferring haplotypes which contribute to autoimmune disease. No class II sequences have been found by the applicants to be uniquely associated with IDDM. That observation suggests that "normal" class II alleles confer susceptibility, or that the susceptibility genes reside elsewhere in the MHC. Given the estimates of penetrance and concordance (50% for monozygetic twins and 25% for HLA identical sibs) for IDDM [Henson et al., Mol. Biol. Med. (1986), 3.129–136], it is not surprising that some unaffected individuals contain putative class II susceptibility genes.

It appears that some environmental "triggering" agent, such as viral infection, is required for the disease to develop in susceptible individuals. The homology between DQβ alleles and rubella, a virus implicated in IDDM pathogenesis suggests a viral triggering mechanism.

Viruses have evolved mechanisms to evade their hosts immune defenses (McChesney et al., supra; Srinivasappa et al., supra), and some of these mechanisms appear to involve mimicry of vital MHC epitopes. The present invention relates to the indentification of regions homology between the HLA-DQ proteins and human viral pathogens. [See Example VI.] Table VII summarizes the major homologies observed to the Epstein-Barr virus (EBV), the genome for which has been completely sequenced. [Baer et al, Nature, 310:207–211.]

TABLE VII

Homologies Between HLA-DQβ Alleles and EBV

| DQβ allele | HLA epitope | EBV homology | pos. | phase | ORF size | ORF name |
|---|---|---|---|---|---|---|
| DQB1.4 (DR2) | GRPDAEY | RPDAE | 167112 | R3 | 101 | BNLF26 |
| DQB2 (DR3) | GLPAAEY | GLPAA | 792 | R1 | 134 |  |
|  |  |  | 67134 | R3 | 188 |  |
|  |  |  | 80004 | R1 | 30 |  |
|  |  |  | 118884 | R3 | 57 |  |
|  |  |  | 134232 | F1 | 72 |  |
|  |  | PAAEY | 73713 | R3 | 1374 | BOLF1 |
| DQB3.2 (DR4) | GPPAAEY | GPPAA | 12404* | F1 | 129 | BWRF1 |
|  |  |  | 61311 | R1 | 20 |  |
|  |  |  | 100137** | F3 | 872 | BERF4 |
|  |  |  | 100257 | F3 | 872 | BERF4 |
|  |  | PPAAEY | 73713 | R3 | 1374 | BOLF1 |

*(repeated 12 times as part of the 3072 bp 'IR1' repeat)
**(directly repeated 6 times)

Only one homology was seen between the peptide and potential epitope centered at position 57 in the DQB1.4 (DR2) allele and the entire EBV genome. However, six matches were seen to the peptide from the DRB2 (DR3) allele, and 21 were seen to the GPPAA peptide from the DQB3.2 (DR4) allele. Many of the later homologies were found in repeated segments of the EBV genome, including one segment of five amino acids directly repeated six times. In addition, the E1 envelope protein of rubella [Nakhasi et al., J. Biol. Chem., (1986), 261:16616–16621], a virus implicated in IDDM pathogenesis [Rubenstein et al., Diabetes, (1982), 31:1088–1091], contains the GPPAA peptide at position 261. Exposure of a fetus to the rubella virus leads to a congenital infection, and a high risk for diabetes. Based on the homology between viral pathogens (such as EBV and rubella) and the DQβ peptide Gly Pro Pro Ala Glu, such region could also serve as a target for molecular mimicry [Oldstone et al., supra] with an immune response to an infecting virus possibly leading to an attack on self cells.

Further, viruses other than EBV and rubella have been implicated with IDDM such as Coxsackie and cytomegalovirus (CtIV) (Yoon et al., supra).

The viruses are likely mimicking HLA class II genes, and in particular the HLA DQβ genes around codon 57, delaying or modifying the onset of an effective immune response. If the immune system actually responds to the mimicked HLA epitope, then normal regulation of the immune system could be perturbed, possible leading to autoimmune disease Autoimmune disease could result from a series of factors: 1) inheritance of HLA alleles which are being mimicked by viruses, 2) infection by a virus mimicking the host's HLA class II alleles, 3) an immune response by the host to the mimicked epitopes, 4) perturbation of immune regulation of autoimmune responses, 5) development of an autoimmune response, and 6) progressive tissue destruction leading to an autoimmune disease.

An example of this mechanism could involve a person inheriting the DQB3.2 allele correlating with increased risk to IDDM followed by infection by the rubella virus, which is also correlated with IDDM, and which contains an epitope in its E1 envelope protein which specifically mimics a portion of the DQB3.2 protein. After infection by the virus, the person may elicit an immune response involving antibodies or T cells directed against the El protein, and cross-reactive to the DQB3.2 protein. This antibody or T cell response interferes with the normal function of the HLA DQ protein, eading to an autoimmune response and IDDM. The target of the final utoimmunity may be determined by the location of the viral infection, in this case the beta cells of the islets of Langerhans. Increased degrees of risk could be ascertained as an individual is shown to have the DQB3.2 allele, followed by infection by the rubella virus, followed by the appearance of anti-rubella antibodies cross-reactive to the HLA DQ-beta protein.

Diagnostic tests to determine whether an individual with alleles associated with an autoimmune susceptibility has been infected by a virus correspondingly associated with susceptibility to an autoimmune disease (based on the virus having homology to segments of the HLA class II alleles) could be used to determine an effective prophylactic or therapeutic treatment plan for such individual. For example, vaccines, immunotoxins, immuno-antigens, peptides corresponding to the epitope of the mimicked region, or anti-idiotype antibodies could then be used to prevent or reverse an immune response against epitopes presented by the pathogenic organisms.

An example of such a diagnostic test could be detecting an immune response (i.e., antibody production or reactive immune cells) as reported in Schwinnbeck et al., *J. Exp. Med.*, 166:173–181 (1987), where antibodies against a portion of the class I HLA molecule B27 are detected by attaching a synthetic peptide to a solid support, treating it with a dilution of the test serum, washing the solid support, and then testing whether any antibodies are retained. Other examples of such a diagnostic test could be either by directly probing for the viral DNA genome, as is done with the HIV (AIDS) virus, in Kwok et al., *J. Virol.*, 61:1690–1694 (1987), or by indirectly assaying for antibodies arising from infection, as in agglutination tests for CMV antibodies.

Dw4

The DR4, Dw10 DRβI allele is associated with susceptibility to both PV and to IDDM. That allele contains the nucleotide sequence which encodes the I-DE amino acid sequence in the third hypervariable region (HV3; segment D in FIG. 5) around positions 68–72 of the DRβI chain. Another DR4 DRβI allele, Dw4, also polymorphic in the same hypervariable region (HV3; segment D in FIG. 5), has the sequence GGAGCAGAAGCGGGCCGCG around positions 68–72, and is also associated with IDDM. Thus, most DR4+IDDM patients are either DR4, Dw4 or DR4, Dw10, indicating that both the DQβ allelic variants (see above) and the DRβI allelic variants contribute to autoimmunity. The Dw4 variant can be distinguished from the other DR4, DRβI alleles by sequence specific oligonucleotide (SSO) analysis.

The DR4 haplotype, Dw4 subtype is also associated with rheumatoid arthritis (RA), as is DR4, Dw14. [Roudier et al., Abstract from American Rheumatism Association (Western Region) meeting in San Diego, Calif., Nov. 5–7, 1987, page 15.] A hexapeptide from the HV3 region of the DRβI chain at amino acids 69–74, that distinguishes Dw4 from the other DR4, DRβI alleles is shared by the Epstein-Barr virus (EBV) open reading frame BALF4 and may serve as a target for molecular mimicry.

Detection Means

The above-mentioned DNA sequences may be detected by DNA hybridization probe technology. In one example, which is not exclusive, the sample suspected of containing the genetic marker is spotted directly on a series of membranes and each membrane is hybridized with a different labeled oligonucleotide probe that is specific for the particular sequence variation. One procedure for spotting the sample on a membrane is described by Kafotos et al., *Nucleic Acids Research*, 7:1541–1552 (1979).

Briefly, the DNA sample affixed to the membrane may be pretreated with a prehybridization solution containing sodium dodecyl sulfate, Ficoll, serum albumin and various salts prior to the probe being added. Then, a labeled oligonucleotide probe that is specific to each sequence to be detected is added to a hybridization solution similar to the prehybridization solution. The hybridization solution is applied to the membrane and the membrane is subjected to hybridization conditions that will depend on the probe type and length, type and concentration of ingredients, etc. Generally, hybridization is carried out at about 25–75° C., preferably 35 to 65° C., for 0.25–50 hours, preferably less than three hours. The greater the stringency of conditions, the greater the required complementarity for hybridization between the probe and sample. If the background level is high, stringency may be increased accordingly. The stringency can also be incorporated in the wash.

After the hybridization the sample is washed of unhybridized probe using any suitable means such as by washing one or more times with varying concentrations of standard saline phosphate EDTA (SSPE) (180 nM NaCl, 10 mM $Na_2HPO_4$ and 1 M EDTA, pH 7.4) solutions at 25–75° C. for about 10 minutes to one hour, depending on the temperature. The label is then detected by using any appropriate detection techniques.

The sequence-specific oligonucleotide that may be employed herein is an oligonucleotide that may be prepared using any suitable method, such as, for example, the organic synthesis of a nucleic acid from nucleoside derivatives. This synthesis may be performed in solution or on a solid support. One type of organic synthesis is the phosphotriester method, which has been utilized to prepare gene fragments or short genes. In the phosphotriester method, oligonucleotides are prepared that can then be joined together to form longer nucleic acids. For a description of this method, see Narang, S. A., et al., *Meth. Enzymol.*, 68, 90 (1979) and U.S. Pat. No. 4,356,270. The patent describes the synthesis and cloning of the somatostatin gene.

A second type of organic synthesis is the phosphodiester method, which has been utilized to prepare tRNA gene. See Brown, E. L., et al., *Meth. Enzymol.*, 68, 109 (1979) for a description of this method. As in the phosphotriester method, the phosphodiester method involves synthesis of oligonucleotides that are subsequently joined together to form the desired nucleic acid.

Automated embodiments of these methods may also be employed. In one such automated embodiment diethylphosphoramidites are used as starting materials and may be synthesized as described by Beaucage et al., *Tetrahedron Letters*, 22:1859–1862 (1981). One method for synthesizing oligonucleotides on a modified solid support is described in U.S. Pat. No. 4,458,066. It is also possible to use a primer which has been isolated from a biological source (such as a restriction endonuclease digest).

The sequence-specific oligonucleotide must encompass the region of the sequence which spans the nucleotide variation being detected and must be specific for the nucleotide variation being detected. For example, four oligonucleotides may be prepared, each of which contains the nucleotide sequence site characteristic of each of the four DNA sequences herein. Each oligonucleotide would be hybridized to duplicates of the same sample to determine whether the sample contains one or more of the regions of the locus where allelic variations may occur which are characteristic of IDDM or PV.

The length of the sequence-specific oligonucleotide will depend on many factors, including the source of oligonucleotide and the nucleotide composition. For purposes herein, the oligonucleotide typically contains 15–25 nucleotides, although it may contain more or fewer nucleotides. While oligonucleotides which are at least 19-mers in length may enhance specificity and/or sensitivity, probes which are less than 19-mers, e.g., 16-mers, show more sequence-specific discrimination, presumably because a single mismatch is more destabilizing. If amplification of the sample is carried out as described below prior to detection with the probe, amplification increases specificity so that a longer probe length is less critical, and hybridization and washing temperatures can be lowered for the same salt concentration. Therefore, in such as case it is preferred to use probes which are less than 19-mers.

Where the sample is first placed on the membrane and then detected with the oligonucleotide, the oligonucleotide must be labeled with a suitable label moiety, which may be detected by spectroscopic, photochemical, biochemical, immunochemical or chemical means. Immunochemical means include antibodies which are capable of forming a complex with the oligonucleotide under suitable conditions, and biochemical means include polypeptides or lectins capable of forming a complex with the oligonucleotide under the appropriate conditions. Examples include fluorescent dyes, electron-dense reagents, enzymes capable of depositing insoluble reaction products or being detected chronogenically, such as alkaline phosphatase, a radioactive label such as $^{32}$p, or biotin. If biotin is employed, a spacer arm may be utilized to attach it to the oligonucleotide. Preferably, the labels used are non-radioactive.

In a "reverse" dot blot format, a labeled sequence-specific oligonucleotide probe capable of hybridizing with one of the DNA sequences is spotted on (affixed to) the membrane under prehybridization conditions as described above. The sample is then added to the pretreated membrane under hybridization conditions as described above. Then the labeled oligonucleotide or a fragment thereof is released from the membrane in such a way that a detection means can be used to determine if a sequence in the sample hybridized to the labeled oligonucleotide. The release may take place, for example, by adding a restriction enzyme to the membrane which recognizes a restriction site in the probe. This procedure, known as oligomer restriction, is described more fully in EP Patent Publication 164,054 published Dec. 11, 1985, the disclosure of which is incorporated herein by reference.

Alternatively, a sequence specific oligonucleotide immobilized to the membrane could bind or "capture" a target DNA strand (PCR-amplified). This "captured" strand could be detected by a second labeled probe. The second oligonucleotide probe could be either locus-specific or allele-specific.

In an alternative method for detecting the DNA sequences herein, the sample to be analyzed is first amplified using DNA polymerase, four nucleotide triphosphates and two primers. Briefly, this amplification process involves the steps of:

(a) treating a DNA sample suspected of containing one or more of the four IDDM genetic marker sequences, together or sequentially, with four different nucleotide triphosphates, an agent for polymerization of the nucleotide triphosphates, and one deoxyribonucleotide primer for each strand of each DNA suspected of containing the IDDM or PV genetic markers under hybridizing conditions, such that for each DNA strand containing each different genetic marker to be detected, an extension product of each primer is synthesized which is complementary to each DNA strand, wherein said primer(s) are selected so as to be substantially complementary to each DNA strand containing each different genetic marker, such that the extension product synthesized from one primer, when it is separated from its complement, can serve as a template for synthesis of the extension product of the other primer;

(b) treating the sample under denaturing conditions to separate the primer extension products from their templates if the sequence(s) to be detected are present; and (c) treating the sample, together or sequentially, with said four nucleotide triphosphates, an agent for polymerization of the nucleotide triphosphates, and oligonucleotide primers such that a primer extension product is synthesized using each of the single strands produced in step (b) as a template, wherein steps (b) and (c) are repeated a sufficient number of times to result in detectable amplification of the nucleic acid containing the sequence(s) if present.

The sample is then affixed to a membrane and detected with a sequence-specific probe as described above. Preferably, steps (b) and (c) are repeated at least five times, and more preferably 15–30 times if the sample contains human genomic DNA. If the sample comprises cells, preferably they are heated before step (a) to expose the DNA therein to the reagents. This step avoids extraction of the DNA prior to reagent addition.

In a "reverse" dot blot format, at least one of the primers and/or at least one of the four nucleotide triphosphates used in the amplification chain reaction is labeled with a detectable label, so that the resulting amplified sequence is labeled. These labeled moieties may be present initially in the reaction mixture or added during a later cycle. Then an unlabeled sequence-specific oligonucleotide capable of hybridizing with the amplified sequence(s), if the sequence (s) is/are present, is spotted on (affixed to) the membrane under prehybridization conditions as described above. The amplified sample is then added to the pretreated membrane under hybridization conditions as described above. Finally, detection means are used to determine if an amplified sequence in the DNA sample has hybridized to the oligonucleotide affixed to the membrane. Hybridization will occur only if the membrane-bound sequence containing the variation is present in the amplification product.

As indicated above, variations of this method include use of an unlabeled PCR target, an unlabeled immobilized allele-specific probe and a labeled oligonucleotide probe in a sandwich assay.

The amplification method provides for improved specificity and sensitivity of the probe; an interpretable signal can be obtained with a 0.04 $\mu$g sample in six hours. Also, if the amount of sample spotted on a membrane is increased to 0.1–0.5 $\mu$g, non-isotopically labeled oligonucleotides may be utilized in the amplification process rather than the radioactive probes used in previous methods. Finally, as mentioned above, the amplification process is applicable to use of sequence-specific oligonucleotides less than 19-mers in size, thus allowing use of more discriminatory sequence-specific oligonucleotides.

In a variation of the amplification procedure, a thermostable enzyme, such as one purified from Thermus aquaticus, may be utilized as the DNA polymerase in a temperature-cycled chain reaction. The thermostable enzyme refers to an enzyme which is stable to heat and is heat resistant and catalyzes (facilitates) combination of the nucleotides in the proper manner to form the primer extension products that are complementary to each DNA strand.

In this latter variation of the technique, the primers and nucleotide triphosphates are added to the sample, the mixture is heated and then cooled, and then the enzyme is added, the mixture is then heated to about 90–100° C. to denature the DNA and then cooled to about 35–40° C., and the cycles are repeated until the desired amount of amplification takes place. This process may also be automated. The amplification process using the thermostable enzyme is described more fully in copending U.S. application Ser. Nos. 899,513, abandoned and 063,647, U.S. Pat. No. 4,965,188, filed respectively Aug. 22, 1986 and Jun. 17, 1987, entitled "Process for Amplifying, Detecting, and/or Cloning Nucleic Acid Sequences Using a Thermostable Enzyme," the disclosures of which are incorporated herein by reference.

The invention herein also contemplates a kit format which comprises a packaged multicontainer unit having containers for each labeled sequence-specific DNA probe. The kit may optionally contain a means to detect the label (such as an avidin-enzyme conjugate and enzyme substrate and chromogen if the label is biotin). In addition, the kit may include a container that has a positive control for the probe containing one or more DNA strands with the sequence to be detected and a negative control for the probe that does not contain the DNA strands having any of the sequences to be detected.

One method for detecting the amino acid sequences in a protein sample that are associated with IDDM or PV involves the use of an immunoassay employing one or more antibodies that bind to one or more of the four amino acid sequences. While the antibodies may be polyclonal or monoclonal, monoclonal antibodies are preferred in view of their specificity and affinity for the antigen.

Polyclonal antibodies may be prepared by well-known methods which involve synthesizing a peptide containing one or more of the amino acid sequences associated with IDD,I or PV, purifying the peptide, attaching a carrier protein to the peptide by standard techniques, and injecting a host such as a rabbit, rat, goat, mouse, etc. with the peptide. The sera are extracted from the host by known methods and screened to obtain polyclonal antibodies which are specific to the peptide immunogen. The peptide may be synthesized by the solid phase synthesis method described by Merrifield, R. B., *Adv. Enzymol. Relat. Areas Mol. Biol.,* 32:221–296 (1969) and in "The Chemistry of Polypeptides" (P. G. Katsoyannis, ed.), pp. 336–361, Plenum, New York (1973), the disclosures of which are incorporated herein by reference. The peptide is then purified and may be conjugated to keyhold limpet hemocyanin (KLH) or bovine serum albumin (BSA). This may be accomplished via a sulfhydryl group, if the peptide contains a cysteine residue, using a heterobifunctional crosslinking reagent such as N-maleimido-6-amino caproyl ester of 1-hydroxy-2-nitrobenzene-4-sulfonic acid sodium salt.

The monoclonal antibody will normally be of rodent or human origin because of the availability of murine, rat, and human tumor cell lines that may be used to produce immortal hybrid cell lines that secrete monoclonal antibody. The antibody may be of any isotype, but is preferably an IgG, IgM or IgA, most preferably an IgG2a.

The murine monoclonal antibodies may be produced by immunizing the host with the peptide mentioned above. The host may be inoculated intraperitoneally with an immunogenic amount of the peptide and then boosted with similar amounts of the immunogenic peptide. Spleens or lymphoid tissue is collected from the immunized mice a few days after the final boost and a cell suspension is prepared therefrom for use in the fusion.

Hybridomas may be prepared from the splenocytes or lymphoid tissue and a tumor (myeloma) partner using the general somatic cell hybridization technique of Koehler, B. and Milstein, C., *Nature,* 256:495–497 (1975) and of Koehler, B. et al., *Eur. J. Immunol.,* 6:511–519 (1976). Preferred myeloma cells for this purpose are those which fuse efficiently, support stable, high-level expression of antibody by the selected antibody-producing cells, and are sensitive to a medium such as HAT medium. Among these, preferred myeloma cell lines are murine myeloma lines, such as those derived from MOPC-21 and MOPC-11 mouse tumors available from the Salk Institute, Cell Distribution Center, San Diego, Calif., USA, or P3X63-Ag8.653 (653) and Sp2/0-Ag14 (SP2/0) myeloma lines available from the American Type Culture Collection, Rockville, Md., USA, under ATCC CRL Nos. 1580 and 1581, respectively.

Basically, the technique involves fusing the appropriate tumor cells and splenocytes or lymphoid tissue using a fusogen such as polyethylene glycol. After the fusion the cells are separated from the fusion medium and grown on a selective growth medium, such as HAT medium, to eliminate unhybridized parent cells and to select only those hybridomas that are resistant to the medium and immortal. The hybridomas may be expanded, if desired, and supernatants may be assayed by conventional immunoassay procedures (e.g., radioimmunoassay, enzyme immunoassay, or fluorescence immunoassay) using the immunizing agent as antigen. Positive clones may be characterized further to determine whether they meet the criteria of the antibodies of the invention. For example, the antigen-binding ability of the antibodies may be evaluated in vitro by immunoblots, ELISAs and antigen neutralizing tests.

A preferred procedure for making a hybrid cell line that secretes human antibodies against the amino acid genetic markers is somatic cell hybridization using a mouse x human parent hybrid cell line and a human cell line producing sufficiently high levels of such antibodies. The human cell line may be obtained from volunteers immunized with the peptide(s) described above. The human cell line may be transformed with Epstein-Barr virus (EBV) as described, for example, by Foung, et al., *J. Immunol. Methods,* 70:83–90 (1984).

When EBV transformation is employed, the most successful approaches have been either to pre-select the population of B cells to be transformed or to post-select the antigen-specific transformed populations by panning or rosetting techniques, as described by Kozbar, et al., *Scan. J. Immunol.,* 10:187–194 (1979) and Steinitz, et al., *J. Clin. Lab. Immun.,* 2:1–7 (1979). Recently EBV transformation has been combined with cell fusion to generate human monoclonal antibodies (see, e.g., Foung et al., *J. Immun. Meth.,* 70:83–90 (1984)), due to instability of immunoglobulin secretion by hybridomas when compared to EBV lymphoblastoid cell lines, and higher frequencies of rescue of the antigen-specific populations. EBV most frequently infects and transforms IgM-bearing B cells, but B cells secreting other classes of Ig can also be made into long-term lines using the EBV fusion technique, as described by Brown and Miller, *J. Immunol.,* 128:24–29 (1982).

The cell lines which produce the monoclonal antibodies may be grown in vitro in suitable culture medium such as Iscove's medium, Dulbecco's Modified Eagle's Medium, or RPMI-1640 medium from Gibco, Grand Island, N.Y., or in vivo in syngeneic or immunodeficient laboratory animals. If desired, the antibody may be separated from the culture medium or body fluid, as the case may be, by conventional techniques such as ammonium sulfate precipitation, hydroxyapatite chromatography, ion exchange chromatography, affinity chromatography, electrophoresis, microfiltration, and ultracentrifugation.

The antibodies herein may be used to detect the presence or absence of one or more of the four amino acid sequences associated with IDDM in white blood cells expressing the HLA class II antigens. The cells may be incubated in the presence of the antibody, and the presence or absence and/or degree of reaction (antibody-peptide binding) can be determined by any of a variety of methods used to determine or quantitate antibody/antigen interactions (e.g., fluorescence, enzyme-linked immunoassay (ELISA), and cell killing using antibody and complement by standard methods). The antibody employed is preferably a monoclonal antibody.

For use in solid phase immunoassays, the antibodies employed in the present invention can be immobilized on any appropriate solid test support by any appropriate technique. The solid test support can be any suitable insoluble carrier material for the binding of antibodies in immunoassays. Many such materials are known in the art, including, but not limited to, nitrocellulose sheets or filters; agarose, resin, plastic (e.g., PVC or polystyrene) latex, or metal beads; plastic vessels; and the like. Many methods of immobilizing antibodies are also known in the art. See, e.g., Silman et al., *Ann. Rev. Biochem.,* 35:873 (1966); Melrose, Rev. Pure & App. Chem., 21:83 (1971); Cuatrecafas, et al., *Meth. Enzym., Vol.* 22 (1971). Such methods include covalent coupling, direct adsorption, physical entrapment, and attachment to a protein-coated surface. In the latter method, the surface is first coated with a water-insoluble protein such as zein, collagen, fibrinogen, keratin, glutelin, etc. The antibody is attached by simply contacting the protein-coated surface with an aqueous solution of the antibody and allowing it to dry.

Any combination of support and binding technique which leaves the antibody immunoreactive, yet sufficiently immobilizes the antibody so that it can be retained with any bound antigen during a washing, can be employed in the present invention. A preferred solid test support is a plastic bead.

In the sandwich immunoassay, a labeled antibody is employed to measure the amount of antigen bound by the immobilized monoclonal antibody. The label can be any type that allows for the detection of the antibody when bound to a support. Generally, the label directly or indirectly results in a signal which is measurable and related to the amount of label present in the sample. For example, directly measurable labels can include radiolabels (e.g., $^{125}I$, $^{35}S$, $^{14}C$, etc.). A preferred directly measurable label is an enzyme, conjugated to the antibody, which produces a color reaction in the presence of the appropriate substrate (e.g., horseradish peroxidase/o-phenylenediamine). An example of an indirectly measurable label would be antibody that has been biotinylated. The presence of this label is measured by contacting it with a solution containing a labeled avidin complex, whereby the avidin becomes bound to the biotinylated antibody. The label associated with the avidin is then measured. A preferred example of an indirect label is the avidin/biotin system employing an enzyme conjugated to the avidin, the enzyme producing a color reaction as described above. It is to be understood, however, that the term "label" is used in its broadest sense and can include, for example, employing "labeled" antibodies where the label is a xenotypic or isotypic difference from the immobilized antibody, so that the presence of "labeled" antibodies is detectable by incubation with an anti-xenotypic or anti-isotypic antibody carrying a directly detectable label.

Whatever label is selected, it results in a signal which can be measured and is related to the amount of label in a sample. Common signals are radiation levels (when radioisotopes are used), optical density (e.g., when enzyme color reactions are used), and fluorescence (when fluorescent compounds are used). It is preferred to employ a nonradioactive signal, such as optical density (or color intensity) produced by an enzyme reaction. Numerous enzyme/substrate combinations are known in the immunoassay art which can produce a suitable signal. See, e.g., U.S. Pat. Nos. 4,323,647 and 4,190,496, the disclosures of which are incorporated herein.

For diagnostic use, the antibodies will typically be distributed in multicontainer kit form. These kits will typically contain the antibody(ies) in labeled or unlabeled form in suitable containers, any detectable ligand reactive with unlabeled antibody if it is used, reagents for the incubations and washings if necessary, reagents for detecting the label moiety to be detected, such as substrates or derivatizing agents depending on the nature of the label, product inserts and instructions, and a positive control associated with IDDM or PV, such as a cell containing the HLA class II antigens associated with IDDM or PV. The antibodies in the kit may be affinity purified if they are polyclonal.

The following examples illustrate various embodiments of the invention and are not intended to be limiting in any respect. In the examples all parts and percentages are by weight if solid and by volume if liquid, and all temperatures are in degrees Centigrade, unless otherwise indicated.

EXAMPLE I

This example illustrates how four DR-β sequences associated with IDDM were identified.

I. Analysis of HLA-DR-β Sequences

Several HLA class II beta genes were isolated from clinical blood samples of diverse HLA-typed IDDM individuals (from University of Pittsburgh clinic and from cell lines from IDDM patients available from the Human Genetic Mutant Cell Repository, Camden, N.J.) and non-diabetic controls (homozygous typing cells) using cloning methods. In one such method, which is a standard method, human genomic DNA was isolated from the patient samples using essentially the method of Maniatis et al., *Molecular Cloning: A Laboratory Manual* (1982), 280–281 or prepared from the buffy coat fraction, which is composed primarily of peripheral blood lymphocytes, as described by Saiki et al., *Bio/Technology,* 3:1008–1012 (1985). This DNA was then cloned as full genomic libraries into bacteriophage vectors, as described in Maniatis, supra, pp. 269–294. Individual clones for the HLA-DRβ genes were selected by hybridization to radioactive cDNA probes (Maniatis et al., pp. 309–328) and characterized by restriction mapping. See U.S. Pat. No. 4,582,788 issued Apr. 15, 1986. Individual clones from IDDM patients were assigned to DR-typed haplotypes by comparing the clone restriction map with the RFLP segregation pattern within the patients' family. Finally, small fragments of these clones representing the variable second exon were subcloned (Maniatis, pp. 390–402) into the M13mp10 cloning vector, which is publicly available from Boehringer-Mannheim.

In an alternative procedure for cloning the genes, amplification of the relevant portion (the second exon) of the gene was carried out as described below.

A total of 1 microgram of each isolated human genomic DNA was amplified in an initial 100 μl reaction volume containing 10 μl of a solution containing 100 mM Tris.HCl buffer (pH 7.5), 500 mM NaCl, and 100 mM MgCl$_2$, 10 μl of 10 μM of primer GH46, 10 μl of 10 μM of primer GH50, 15 μl of 40 mM dNTP (contains 10 mM each of dATP, dCTP, dGTP and TTP), and 45 μl of water. Primers GH46 and GH50 have the following sequences:

5'-CCGGATCCTTCGTGTCCCCACAGCACG-3' (GH46)

5'-CTCCCCAACCCCGTAGTTGTGTCTGCA-3' (GH50)

These primers, having non-homologous sequences to act as linker/primers, were prepared as follows:

A. Automated Synthesis Procedures: The diethylphosphoramidites, synthesized according to Beaucage and Caruthers (*Tetrahedron Letters* (1981) 22:1859–1862) were sequentially condensed to a nucleoside derivatized controlled pore glass support using a Biosearch SAM-1. The procedure included detritylation with trichloroacetic acid in dichloromethane, condensation using benzotriazole as activating proton donor, and capping with acetic anhydride and dimethylaminopyridine In tetrahydrofuran and pyridine. Cycle time was approximately 30 minutes. Yields at each step were essentially quantitative and were determined by collection and spectroscopic examination of the dimethoxytrityl alcohol released during detritylation.

B. Oligodeoxyribonucleotide Deprotection and Purification Procedures: The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia was removed and the residue was applied to a preparative polyacrylamide gel. Electrophoresis was carried out at 30 volts/cm for 90 minutes after which the band containing the product was identified by UV shadowing of a fluorescent plate. The band was excised and eluted with 1 ml distilled water overnight at 4° C. This solution was applied to an Altech RP18 column and eluted with a 7–13% gradient of acetonitrile in 1% ammonium acetate buffer at pH 6.0. The elution was monitored by UV absorbance at 260 nm and the appropriate fraction collected, quantitated by UV absorbance in a fixed volume and evaporated to dryness at room temperature in a vacuum centrifuge.

C. Characterization of Oligodeoxyribonucleotides: Test aliquots of the purified oligonucleotides were $^{32}$p labeled with polynucleotide kinase and γ-$^{32}$P-ATP. The labeled compounds were examined by autoradiography of 14–20% polyacrylamide gels after electrophoresis for 45 minutes at 50 volts/cm. This procedure verifies the molecular weight. Base composition was determined by digestion of the oligodeoxyribonucleotide to nucleosides by use of venom diesterase and bacterial alkaline phosphatase and subsequent separation and quantitation of the derived nucleosides using a reverse phase HPLC column and a 10% acetonitrile, 1% ammonium acetate mobile phase.

The above reaction mixtures were held in a heat block set at 95° C. for 10 minutes to denature the DNA. Then each DNA sample underwent 28 cycles of amplification, where each cycle was composed of four steps:

(1) spinning the sample briefly (10–20 seconds) in microcentrifuge to pellet condensation and transfer the denatured material immediately to a heat block set at 30° C. for two minutes to allow primers and genomic DNA to anneal, (2) adding 2 μl of a solution prepared by mixing 39 μl of the Klenow fragment of *E. coli* DNA Polymerase I (New England Biolabs, 5 units/μl), 39 μl of a salt mixture of 100 mM Tris buffer (pH 7.5), 500 mM NaCl and 100 mM MgCl$_2$, and 312 μl of water, (3) allowing the reaction to proceed for two minutes at 30° C., and (4) transferring the samples to the 95° C. heat block for two minutes to denature the newly synthesized DNA, except this reaction was not carried out at the last cycle.

Then the mixtures were stored at −20° C. The following cloning procedure was used for the amplified products.

The reaction mixture was sub-cloned into M13mp10 by first digesting in 50 μl of a buffer containing 50 mM NaCl, 10 mM Tris.HCl, pH 7.8, 10 mM MgCl$_2$, 20 units PstI, and 26 units HindIII at 37° C. for 90 minutes. The reaction was stopped by freezing. The volume was adjusted to 110 μl with a buffer containing Tris.HCl and EDTA and loaded onto a 1 ml BioGel P-4 spin dialysis column. One fraction was collected and ethanol precipitated.

The ethanol pellet was resuspended in 15 μl water and adjusted to 20 μl volume containing 50 mM Tris.HCl, pH 7.8, 10 mM MgCl$_2$, 0.5 mM ATP, 10 mM dithiothreitol, 0.5 μg of M13mp10 vector digested with PstI and HindIII and 400 units ligase. This mixture was incubated for three hours at 16° C.

Ten microliters of ligation reaction mixture containing Molt 4 DNA was transformed into *E. coli* strain JM103 competent cells, which are publicly available from BRL in Bethesda, Md. The procedure followed for preparing the transformed strain is described in Messing, J. (1981) *Third Cleveland Symposium on Macromolecules:Recombinant DNA*, ed. A. Walton, Elsevier, Amsterdam, 143–153.

About 40 different alleles from these two cloning procedures were sequenced. In some of the sequences determined four areas of specific DNA and protein sequence were found to occur in various combinations and to be associated with IDDM. The DNA sequences seen in each of these segments in the genomes of IDDM patients produced an alteration in one to three amino acid residues of the DRβ protein. These four variable segments of the DRβ second exon, found in sequences obtained from many diabetic sources, and labeled A-D, are identified above. The regions which can be used for devising probes used for detecting such sequences are identified in FIG. 5, where the amino acid abbreviations are shown in Table VIII.

TABLE VIII

| Amino Acid Abbreviation Codes | | |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |

TABLE VIII-continued

Amino Acid Abbreviation Codes

| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

II. Preparation of Primers for Detection

Oligonucleotides designated GH46 and GH50 complementary to opposite strands of the conserved 5' and 3' ends of the DR-β second exon were used as primers. The primers have the sequences identified in the section above.

III. Expected Amplification Reaction

One microgram of DNA from each DNA sample to be tested (10 μl of 100 μg/ml DNA) may be amplified in an initial 100 μl reaction volume containing 10 μl of a solution containing 100 mM Tris buffer (pH 7.5), 500 mM NaCl, and 100 mM MgCl$_2$. 10 μl of 10 μM of primer GH46, 10 μl of 10 μM of primer GH50, 15 μl of 40 mM dNTP (contains 10 mM each of dATP, dCTP, dGTP and TTP), 10 μl DMSO, and 45 μl of water.

Each reaction mixture is held in a heat block set at 95° C. for 10 minutes to denature the DNA. Then each DNA sample undergoes 30 cycles of amplification where each cycle is composed of four steps:

(1) spinning the sample briefly (10–20 seconds) in microcentrifuge to pellet condensation and transfer the denatured material immediately to a heat block set at 37° C. for two minutes to allow primers and genomic DNA to anneal, (2) adding 2 pl of a solution prepared by mixing 39 μl of the Klenow fragment of *E. coli* DNA Polymerase I (New England Biolabs, 5 units/μl), 39 μl of a salt mixture of 100 mM Tris buffer (pH 7.5), 500 mM NaCl and 100 mM MgCl$_2$, and 312 μl of water, (3) allowing the reaction to proceed for two minutes at 37° C., and (4) transferring the samples to the 95° C. heat block for two minutes to denature the newly synthesized DNA, except this reaction was not carried out at the last cycle.

The final reaction volume is 150 μl, and the reaction mixture is stored at −20° C.

IV. Expected Synthesis and Phosphorylation of Oligodeoxyribonucleotide Probes

Two of four labeled DNA probes, designated GH54 (V--S) and GH78 (I--DE), from Regions C and D, respectively, are employed.

These two probes are synthesized according to the procedures described above for preparing primers for cloning. The probes are labeled by contacting 10 pmole thereof with 4 units of T4 polynucleotide kinase (New England Biolabs) and about 40 pmole $\gamma^{-32}$ p-ATP (New England Nuclear, about 7000 Ci/mmole) In a 40 μl reaction volume containing 70 mM Tris buffer (pH 7.6), 10 mM MgCl$_2$, 1.5 mM spermine, 100 mM dithiothreitol and water for 60 minutes at 37° C. The total volume is then adjusted to 100 μl with 25 mM EDTA and purified according to the procedure of Maniatis et al., *Molecular Cloning* (1982), 466–467 over a 1 ml Bio Gel P-4 (BioRad) spin dialysis column equilibrated with Tris-EDTA (TE) buffer (10 mM Tris buffer, 0.1 mM EDTA, pH 8.0).

V. Expected Dot Blot Hybridizations

Five microliters of each of the 150 μl amplified samples from Section III was diluted with 195 μl 0.4 N NAOH, 25 mM EDTA and spotted onto three replicate Genatran 45 (PLASCO) nylon filters by first wetting the filter with water, placing it in a Bio-Dot (BioRad) apparatus for preparing dot blots which holds the filter in place, applying the samples, and rinsing each well with 0.4 ml of 20×SSPE (3.6 M NaCl, 200 mM NaH$_2$PO$_4$, 20 mM EDTA), as disclosed by Reed and Mann, *Nucleic Acids Research,* 13, 7202–7221 (1985). The filters are then removed, rinsed in 20×SSPE, and baked for 30 minutes at 80° C. in a vacuum oven.

After baking, each filter is then contacted with 6 ml of a hybridization solution consisting of 5×SSPE, 5×Denhardt's solution (1 x=0.02% polyvinylpyrrolidone, 0.02% Ficoll, 0.02% bovine serum albumin, 0.2 mM Tris.HCl, 0.2 mM EDTA, pH 8.0) and 0.5% SDS and incubated for 60 minutes at 55° C. Then 5 μl each of the probes is added to the hybridization solution and the filters are incubated for 60 minutes at 55° C.

Finally, each hybridized filter is washed under stringent conditions. The genotypes are expected to be readily apparent after 90 minutes of autoradiography. The probes are expected to have reasonable specificity for the portions of the allele being detected in genomic DNA samples.

EXAMPLE II

Peptides to the amino acid sequences disclosed may be prepared as described above and used as immunogens to generate antibodies thereto, useful in immunoassays for detecting the amino acid sequence(s) in protein samples.

EXAMPLE III

To explore the possibility that both the DR4 and DRw6 haplotypes which are associated with *Pemphigus vulgaris* (PV) contain a common epitope indicative of PV susceptibility in the DRβI chain, the nucleotide sequences of the polymorphic second exon of the DRβ and DQβ loci from three PV patients were determined. As the HLA-DR serotypes of the three PV patients were DR4/4, DR4/5 and DR4/5, only the issue of DR4 associated PV susceptibility was explored in this example. The sequence analysis was carried out on M13 clones containing specific polymerase chain reaction (PCR) amplified fragments. [See Saiki et al., *Science,* 230:1350–1354 (1985); and Scharf et al., *Science,* 233:1076–1078 (1986) for methodology associated with PCR amplification, cloning and sequence analysis.]

Sample Preparation and Amplification Procedures

Blood samples from three *Pemphigus vulgaris* patients were provided by Dr. Bruce Wintroub, UCSF (California). 0.5 ml of whole blood was lysed by the addition of 1.5 ml of 10 mM Tris, pH 7.5, 10 mM EDTA, 100 mM NaCl, 40 mM dithiothreitol, and 200 μg/ml Proteinase K and incubated for 16 hours at 55° C. The samples were phenol extracted, phenol-CHCl$_3$ and CHCl$_3$ extracted and ethanol precipitated overnight at −20° C. The precipitated DNA was pelleted by centrifugation, washed with 70% ethanol, dried and resuspended in 100 μl 10 mM Tris, 0.1 mM EDTA containing 100 μg/ml RNAse A and incubated at 37° C. for 15 minutes. The DNA samples were re-extracted with phenol-CHCl$_3$ and CHCl$_3$ to inactivate the RNAse A and ethanol precipitated, washed, and dried as described above. 1 μg of intact genomic DNA was amplied by polymerase chain reaction (PCR) (Scharf et al., id.) with the following changes in the reaction conditions: A.) The HLA DRβ region genes were amplified by using 1 μM of the PCR primers GH46 and GH50 (See FIG. 1 for description of primers and the HLA DRβ target fragment); 1 unit of cloned *E. coli* DNA polymerase 1 large fragment (Klenow fragment) was added for 20 cycles of amplification; an additional five cycles of amplification was run on the samples using 4 units of Klenow fragment B.) The HLA DQβ region genes amplified by using 1 μM of PCR primers GH28 and GH29 (such primers are disclosed in copending, commonly owned U.S. application Ser. No. 899,344 filed Aug. 22, 1986):

GH28
(CTCGGATCCGCATGTGCTACTTCACCAACG)
GH29 (GAGCTGCAGGTAGTTGTGTCTGCACAC).

1 unit of Klenow fragment was added for 20 cycles of amplification; an additional 8 cycles of amplification were carried out using 2 units of Klenow fragment per cycle. The DQβ primers produce a 238 base-pair fragment. The DRβ primers produced a 272 bp fragment (see FIG. 1). 1/10 of the PCR reactions were run on a 4% NuSieve, 0.5% SeaKem (FMC) agarose gel and transferred to Genatran 45 nylon membrane (Scharf et al., id.). The filter was prehybridized in 10 ml 5x SSPE, 4x Denhardt's and 0.5% sodium dodecyl sulfate (SDS) for 15 minutes at 37° C. The filter was hybridized with the addition of 0.1 pmole of (γ-$^{32}$P) ATP labeled DRβ specific oligomer GH22 for 16 hours at 37° C. The filter was washed in 4x SSPE, 0.1% SDS for 2.5 minutes at 30° C. and for 1.5 minutes at 37° C. and exposed for 16 hours at −70° C. with one intensifying screen (DuPont Cronex Lightning Plus). The filter was stripped of probe by incubation for five minutes in boiling 0.1x SSPE, 0.1% SDS, dried and prehybridized in 10 ml 6x SSPE, 10x Denhardt's and 0.2% SDS at 42° C. 0.2 pmole of (γ-$^{32}$P) ATP labeled DR4 Dw10 sequence specific oligomer GH78 was added to the prehybridization solution and incubated for 16 hours at 42° C. After hybridization the filter was washed in 1x SSPE, 0.1% SDS for 10 minutes at 37° C. and autoradiographed.

Cloning and Seqencing of HLA DRβ and DQβ PCR Products

One half of each PCR reaction was ethanol precipitated, resuspended and loaded onto a 4% NuSieve, 0.5% SeaKem gel and electrophoresed at 20V-cm for one hour. Slices between 265 and 280 base-pairs for DRβ, and between 220 and 250 base-pairs for DQβ, were removed from the gel and the DNA was electroeluted from the gel in 200 μl 0.5x TBE buffer. The electroeluted DNA samples were dialyzed, digested with 60 units of BamHI and PstI (New England BioLabs) for three hours at 37° C., phenol, phenol-CHCl$_3$ and CHCl$_3$ extracted and ethanol precipitated. One-fourth of the digested PCR DNA was ligated to 200 μg of BamHI/PstI digested, dephosphorylated M13mp10 and transformed into E. coli JM103 and plated onto selective media [Scharf et al., id.; Messing, in Wu et al. (eds), Methods in Enzymology, 101, pp. 20–78 (1983)]. The positive clones were identified by in-situ plaque filter hybridization using a nick-translated DRβ cDNA probe and plaque purified, and DNA from the purified phage clones was sequenced by the chain termination method [Sanger et al., PNAS (USA), 74:5463–5468 (1977].

Analysis

Southern blot analysis of the PCR amplification products and of a DR-3 homozygous typing cell DNA (included as a general DR5 amplification and hybridization control) using a DRβ cDNA probe indicated that all four samples contained roughly equal amounts of amplified DR-beta fragment.

The filter was then stripped of the nick-translated DRβ probe and reprobed with GH78, an oligonucleotide probe specific for the DR4 subtype Dw10 (see FIG. 1). The GH78 sequence specific oligonucleotide (SSO) hybridizes specifically to Dw10 sequences and to none of the other DR4 subtypes (for example, Dw4, Dw14, Dw13 and Dw15). The DNA amplified from all three PV patients hybridized to GH78 but not to the DR-3 homozygous control.

Figure 3:
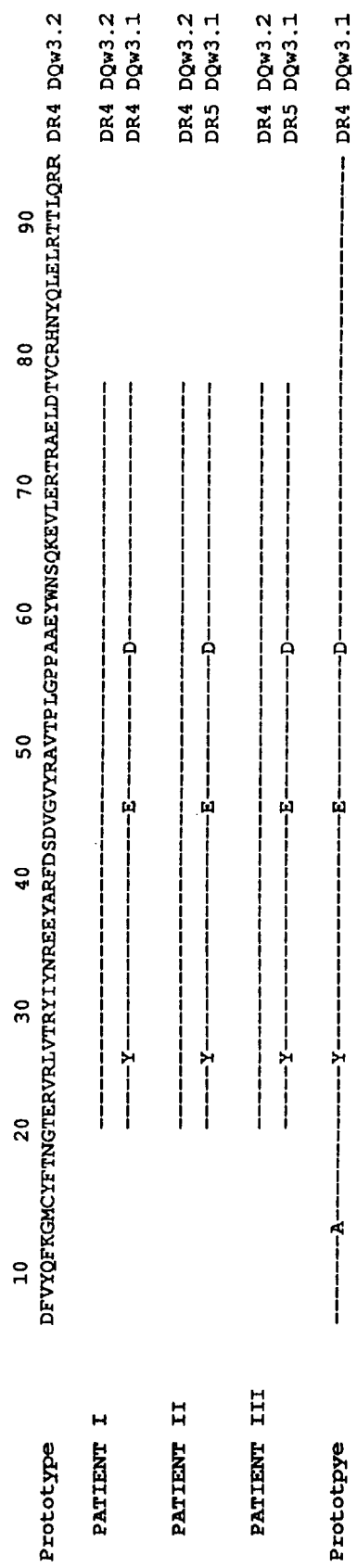
FIG. 3 illustrates the amino acid sequences from the HLA DRβ second exon of three PV patients according to the conventions of FIG. 2 wherein the sequences are aligned with DR4 DQβ 3.1 and DQβ 3.2 prototype sequences from cDNA clones [Michelsen et al., *J. Clin. Invest.*, 79:1144–1152 (1987); Gregersen et al., supra]. At the right of each sequence is the DR type and DQβ type. The DQβ sequences obtained by PCR cloning are shorter than the prototype sequences.

The amplified DNA fragments for the HLA DRβ and DQβ loci were cloned and sequenced to examine in more detail polymorphisms at the level of coding sequences. FIG. 2 shows amino acid alignments derived from nucleotide sequence data for HLA DRβ loci. The DR4 Dw10 subtype prototype sequence is distinguished from the DR4 Dw4 prototype sequence by the substitution of isoleucine, aspartic acid, and glutamic acid (the "I-DE" epitope) for leucine, glutamine, and lysine at amino acid positions 68, 71, and 72, respectively. The sequence alignments show that the DRβ1 sequences from the DR4 alleles of these three patients also contain this "I-DE" epitope). The DRβ1 sequences from the DR5 alleles from the two DR4/5 patients (patients II and III) are identical to the DRβ1 sequence from the DR5 prototype. Likewise, the DRβIII sequences from the DR5 alleles from these two DR4/5 patients are identical to the DR5 DRβIII prototype sequence. Patient I, who is DR4/4, has one Dw10 and one Dw13 halotype, and the DRβIV sequence from this patient is identical to the DR4βIV prototype sequence. The amino acid alignments derived from the nucleotide sequence data for the HLA DQβ loci are shown in FIG. 3. Patient I subtypes as DQB3.2 for one DR4 allele and DQB3.1 for the other DR4 allele. Patients II and III (both DR4/5) are also heterozygous for their DQ5 loci; the DR4 allele is DQB3.2 and the DQB3.1 locus is from the DR5 haplotype. Given the DR serotypes, this heterozygosity at the DQβ locus is not surprising since both DQB3.1 and DQB3.2 are associated with the DR4 haplotype and DQB3.1 is associated with the DR5 halotype. The DQB3.1 and DQB3.2 sequences from all three patients are identical with their respective prototype sequences.

EXAMPLE IV

The same sequence near codon 70 described above in Example III that distinguishes DR4-Dw10 from the other DR4-Dw subtypes is also present on a subset of DRw6 haplotypes. The pattern of sequence polymorphism suggested that this shared "epitope" could be responsible for the DR4 and DRw6 disease association with PV.

DNA samples from Israeli patients, DR-matched controls, and Austrian patients were analyzed with a panel of DRβ and DQβ sequence-specific oligonucleotide probes using PCR amplified DNA in a dot blot format as described above. In the analysis with DRβ-1 oligonucleotide probes, essentially all of the patient DR4 haplotypes (24/24 Israeli patients; 10/14 non-Israeli patients) had the DwlO associated epitope versus a smaller proportion of the control DR4 haplotypes (15/25 Israeli controls; 1/19 non-Israeli controls). However, the proporton of DRw6 DRβ-1 alleles that contain that epitope was lower in DRw6 PV patients (4/14) relative to controls (8/13). Therefore, it was concluded that if the DR4 susceptibility to PV can be attributed to a specific DRβ1 allele, then the DRw6 susceptibility must be accounted for by a different sequence.

EXAMPLE V

PCR Amplification of DQβ Genomic Sequences

To obtain the results shown in FIG. 4, 1 μg of genomic DNA from each of the various cell lines shown in the left-hand side of FIG. 4 was amplified by PCR [Saiki et al., Nature, 324:163–166 (1986)] for 28 cycles with the Klenow fragment of E. coli DNA polymerase. The amplification primers GH28 and GH29 (see Example IV) were used to amplify a 238-bp segment of the DQβ gene. The degree and specificity of amplification were monitored by agarose gel electrophoresis, blotting, and hybridization with $^{32}$P-labeled DQβ cDNA probes (Scharf et al., supra). The sources of the IDDM patients are described in Arnheim et al., supra.

PCR Cloning into M13mp10

The amplified DNA was extracted once with an equal volume of TE-saturated phenol, followed by two extractions with a phenol/chloroform mixture. The DNA was then diluted to 2 ml with sterile water, and dialyzed and concentrated by centrifugation through a Centricon 10 column (Amicon) at 5000×g for 60 minutes at room temperature. In the case of DQβ amplification, where the PCR primers produce a number of non-HLA amplification products, the target band was first cut out of an agarose gel and electroeluted at 100 volts for one hour in 0.5×TBE. The DNA was diluted to 100 μl and digested for two hours at 37° C. with 40 units each of BamHI and PstI. After digestion, the DNA was again phenol/chloroform extracted, dialyzed, and concentrated. It was then ligated into the M13mp10 vector by a modification of the PCR-cloning procedure (Scharf et al., supra). The M13 plaques were initially screened for inserts by hybridization with either DQα or DQβ cDNA probes, and occasionally with allele-specific oligonucleotide (ASO) probes (Saiki et al., supra). These clones were also screened for the amplification products of the DXα or DXβ genes by the use of ASO probes. The single-strand phage DNA was isolated by standard techniques, and sequenced by the dideoxynucleotide primer extension method [Smith, *Meth. Enzymol.*, 65:560–580 (1980)].

EXAMPLE VI

Viral Sequence Homology

The sequence of the 172282-bp genome of strain B95-8 of Epstein-Barr virus (Baer et al., supra) was translated by computer into protein sequences for all six of the forward and reverse phases. These translations were then searched for exact matches of five or more amino acids with polypeptide sequences centered at position 57 of the DQβ alleles (see Table VII). The location and size of the open reading frame (ORF) for each match was then determined, and correlated with the major ORF's and transcriptional segments of the EBV genome (Baer et al, supra). One method of judging the significance of these homologies is by estimating their chance of occurring at random. In the six translation phases of EBV, the amino acid residues near position 57 of the DQβ alleles occur at fractions: A=0.0804, D=0.0258, E=0.0337, G=0.1089, L=0.0890, P=0.1089, R=0.0962, and γ=0.0141. By multiplying these frequencies together, the chances of random occurrence for the polypeptide epitopes are: "RPDAE"=1/1,370,000, "GLPAA"=1/147,000, "PAAEY"=1/2,990,000, "GPPAA"=1/120,000 and "PPAAEY"=1/27,400,000. Thus, since there are 344,560 residues in all six of the translations, we would expect several random occurrences for the "GPPAA" and "GLPAA" epitopes, but none for the others. The excess number of matches and their correlation with major ORF's and with repeated segments of the genome contribute to their significance. By statistical probabilities alone, the six-residue match "PPAAEY" is particularly unlikely to have occurred at random.

Other modifications of the above described embodiments of the invention that are obvious to those skilled in the area of molecular and clinical biology and diagnostics and related disciplines are intended to be within the scope of the following claims.

What is claimed:

1. An oligonucleotide probe fifteen to twenty-five nucleotides in length that is complementary to the second exon of a Class II HLA β-chain gene and comprises a sequence selected from the group consisting of:

(a) 5'-GAGCTGCGTAAGTCTGAG,
(b) 5'-GAGGAGTTCCTGCGCTTC,
(c) 5'-CCTGTCGCCGAGTCCTGG, and a DNA sequence complementary thereto.

2. The DNA probe of claim 1 that is 5'-GAGCTGCGTAAGTCTGAG.

3. The DNA probe of claim 1 that is 5'-GAGGAGTTCCTGCGCTTC.

4. The DNA probe of claim 1 that is 5'-CCTGTCGCCGAGTCCTGG.

5. An oligonucleotide probe fifteen to twenty-five nucleotides in length and complementary to a sequence in the second exon of a Class II HLA β-chain gene that differentiates between the genes present at a higher frequency in individuals susceptible to insulin dependent diabetes mellitus (IDDM) or DR4-associated *Pemphigus vulgaris* and the genes found at higher frequency in non-susceptible individuals.

6. The oligonucleotide of claim 5 that comprises a sequence 5'-GACATCCTGGAAGACGAGCGG, or a DNA sequence complementary thereto.

7. The oligonucleotide of claim 5, wherein said individual is susceptible to DR4, Dw4-associated insulin-dependent diabetes mellitus.

8. The oligonucleotide of claim 5 that comprises a sequence selected from the group consisting of 5'-GACATCCTGGAAGACGAGCGG and a DNA sequence complementary thereto and can be used to identify DR4 Dw10, *Pemphiaus vulgaris*—susceptible individuals.

9. An oligonucleotide probe of claim 5 that differentiates between the DR4 haplotypes DQB3.1 and DQB3.2, said DQB3.1 haplotype being not associated with IDDM susceptibility and said DQB3.2 haplotype being strongly associated with IDDM susceptibility.

10. The DNA probe of claim 6 that is 5'-GACATCCTGGAAGACGAGCGG.

11. The oligonucleotide of claim 7 that comprises the sequence 5'-GGAGCAGAAGCGGGCCGCG, or a DNA sequence complementary thereto.

12. The DNA probe of claim 8 that is 5'-GACATCCTGGAAGACGAGCGG.

13. The oligonucleotide probe of claim 9 that is specific for the DQβ3.1 allele and comprises a sequence 5'-CGTGGAGGTGTACCGGGCG or a sequence complementary thereto.

14. The DNA probe of claim 11 that is 5'-GGAGCAGAAGCGGGCCGCG.

15. The DNA probe of claim 13 that is 5'-CGTGGAGGTGTACCGGGCG.

16. An oligonucleotide probe fifteen to twenty-five nucleotides in length and complementary to a sequence in the second exon of a Class II HLA β-chain gene that differentiates between the genes present at a higher frequency in individuals susceptible to DRw6-associated *Pemphigus vulgaris* and the genes found at a higher frequency in non-susceptible individuals.

17. The oligonucleotide of claim 16 that comprises a nucleotide sequence from a second exon of a DQB1.3 gene in the region from codon 20 to codon 80.

18. An oligonucleotide probe fifteen to twenty-five nucleotides in length and complementary to a sequence in the second exon of a Class II HLA β-chain gene, wherein said probe is complementary to a sequence that comprises codon 57 or to a sequence that identifies codon 57.

19. The oligonucleotide of claim 18, wherein said codon at position 57 is selected from the group consisting of codons for alanine, valine, and aspartate.

20. The oligonucleotide probe of claim 18, wherein said probe does not hybridize to said sequence that comprises codon 57 but instead hybridizes to said DNA sequence that identifies codon 57, wherein said codon is selected from the group consisting of codons for alanine, valine and aspartate.

21. The oligonucleotide of claim 19 that comprises a sequence selected from the group consisting of:
 a) 5'-TCGGCGTCAGGCCGCCCCT;
 b) 5'-TCGGCAACAGGCCGCCCCT; and
a DNA sequence complementary thereto.

22. The oligonucleotide of claim 19 that comprises a sequence selected from the group consisting of:
 (a) 5'-GGGCTGCCTGCCGCC,
 (b) 5'-GGGCGGCCTGTTGCC,
 (c) 5'-GGGCCGCCTGACGCC,
 (d) 5'-GGGCGGCCTGATGCC,
and a DNA sequence complementary thereto.

23. The oligonucleotide of claim 20 that comprises a sequence selected from the group consisting of:
 (a) 5'-GTGGGGGTGTATCGGGCG,
 (b) 5'-GTGGGGGAGTTCCGGGCG,
 (c) 5'-GTGGAGGTGTACCGGGCG,
 (d) 5'-GTGGGGGTGTACCGGGCA,
and a DNA sequence complementary thereto.

24. The DNA probe of claim 21 that is 5'-TCGGCGTCAGGCCGCCCCT.

25. The DNA probe of claim 21 that is 5'-TCGGCAACAGGCCGCCCCT.

26. The DNA probe of claim 22 that is 5'-GGGCTGCCTGCCGCC.

27. The DNA probe of claim 22 that is 5'-GGGCGGCCTGTTGCC.

28. The DNA probe of claim 22 that is 5'-GGGCCGCCTGACGCC.

29. The DNA probe of claim 22 that is 5'-GGGCCGGCCTGATGCC.

30. The oligonucleotide of claim 23 that comprises a sequence selected from the group consisting of:
 a) 5'-CGGCAGGCAGCCCCAGCAG;
 b) 5'-TGTTTGCCTGTTCTCAGAC;
 c) 5'-GATGCTTCTGCTTCACAAGACG;
 d) 5'-GATGTGTCTGGTCACACCCCG;
 e) 5'-TCTTGTAACCAGACACATC; and
a DNA sequence complementary thereto.

31. The DNA probe of claim 23 that is 5'-GTGGGGGTGTATCGGGCG.

32. The DNA probe of claim 23 that is 5'-GTGGGGGAGTTCCGGGCG.

33. The DNA probe of claim 23 that is 5'-GTGGAGGTGTACCGGGCG.

34. The DNA probe of claim 23 that is 5'-GTGGGGGTGTACCGGGCA.

35. The DNA probe of claim 30 that is 5'-CGGCAGGCAGCCCCAGCAG.

36. The DNA probe of claim 30 that is 5'-TGTTTGCCTGTTCTCAGAC.

37. The DNA probe of claim 30 that is 5'-GATGCTTCTGCTTCACAAGACG.

38. The DNA probe of claim 30 that is 5'-GATGTGTCTGGTCACACCCCG.

39. The DNA probe of claim 30 that is 5'-TCTTGTAACCAGACACATC.

40. An oligonucleotide probe fifteen to twenty-five nucleotides in length and complementary to a sequence in the second exon of a Class II HLA DR β-chain gene, wherein said probe is complementary to a polymorphic sequence that can be used to distinguish between DRβ alleles of the DR4 serological type.

* * * * *